(12) United States Patent
Cienfuegos

(10) Patent No.: US 8,744,871 B1
(45) Date of Patent: Jun. 3, 2014

(54) OPERATING SUBFRAME FOR AN INTERFACE MODULE OF AN ILLUMINATED DISPLAY SYSTEM AND METHOD

(76) Inventor: Juan Enrique Cienfuegos, San Antonio, TX (US)

( * ) Notice: Subject to any disclaimer, the term of this patent is extended or adjusted under 35 U.S.C. 154(b) by 593 days.

(21) Appl. No.: 13/098,405

(22) Filed: Apr. 30, 2011

Related U.S. Application Data

(60) Continuation-in-part of application No. 12/589,348, filed on Oct. 22, 2009, now Pat. No. 8,403,846, which is a division of application No. 11/998,951, filed on Dec. 3, 2007, now Pat. No. 7,674,227.

(51) Int. Cl.
*G06Q 10/00* (2012.01)
*G08B 1/08* (2006.01)
*G09F 1/10* (2006.01)

(52) U.S. Cl.
USPC .......... 705/2; 362/231; 235/385; 340/539.12; 340/573.1; 340/815.62

(58) Field of Classification Search
USPC ........... 362/231; 340/573.1, 815.62; 235/385; 705/2, 7; 600/300
See application file for complete search history.

(56) References Cited

U.S. PATENT DOCUMENTS

| | | | |
|---|---|---|---|
| 5,793,882 A | 8/1998 | Piatek et al. | |
| 6,198,394 B1 | 3/2001 | Jacobsen et al. | |
| 6,305,605 B1 * | 10/2001 | Goetz et al. | 235/385 |
| 6,499,658 B2 | 12/2002 | Goetz et al. | |
| 6,761,312 B2 | 7/2004 | Piatek et al. | |
| 7,596,608 B2 | 9/2009 | Alexander et al. | |
| 7,629,881 B2 | 12/2009 | Gao et al. | |
| 8,489,419 B2 * | 7/2013 | Sacco et al. | 705/2 |
| 2008/0017709 A1 * | 1/2008 | Kennedy | 235/385 |
| 2008/0228045 A1 | 9/2008 | Gao et al. | |
| 2008/0300921 A1 * | 12/2008 | Carlton | 705/2 |
| 2009/0018875 A1 | 1/2009 | Monatesti | |
| 2009/0069642 A1 * | 3/2009 | Gao et al. | 600/300 |

* cited by examiner

*Primary Examiner* — Anabel Ton
(74) *Attorney, Agent, or Firm* — Rafael V. Baca; Baca Law Firm, PLLC

(57) ABSTRACT

An interface module for a display interface of an illuminated display system including an operating subframe and a selector coupled to the operating subframe. The operating subframe is coupled to a plurality of light emitters. Each light emitter provides a different predetermined wavelength of light than the other light emitters from the plurality of light emitters. Each respective predetermined wavelength provides information relating to a corresponding predetermined status. Each desired light emitter is chosen from the plurality of light emitters according to a lighting operation sequence. The operating subframe includes a module processor coupled to the plurality of light emitters and the selector, a removable external memory device, and an external memory processor, and a bus coupled to the module processor and the removable external memory processor. The module processor stores illuminated light emitter information in a computer readable format within the removable external memory device.

20 Claims, 14 Drawing Sheets

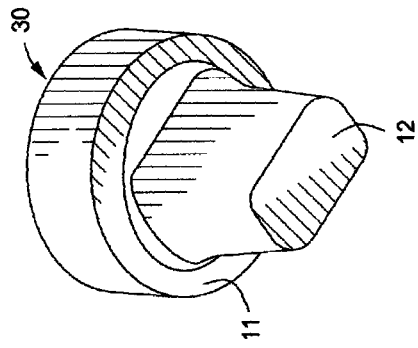
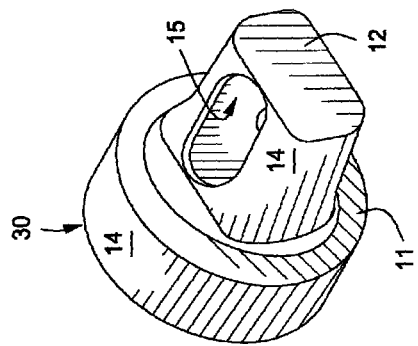
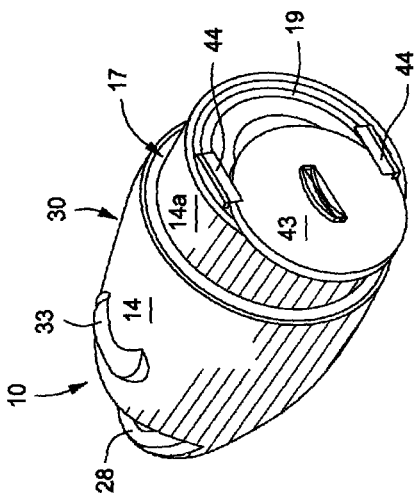

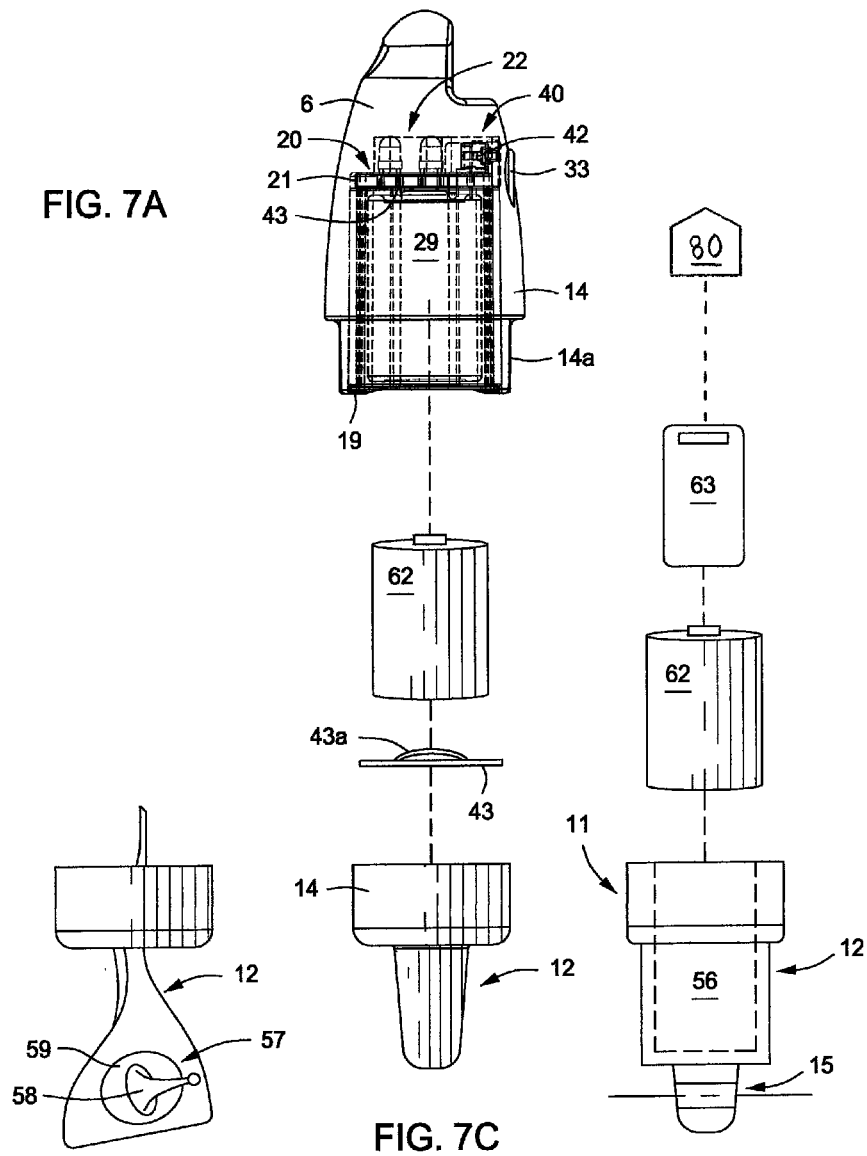

OPERATING SUBFRAME FOR AN INTERFACE MODULE OF AN ILLUMINATED DISPLAY SYSTEM AND METHOD

CROSS REFERENCE TO RELATED APPLICATIONS

This application is a Continuation-in-Part of a Continuation-in-Part application Ser. No. 12/589,348 and claims benefit under 35 U.S.C. §§119, 120, 121, and/or 365 of at least said application Ser No. 12/589,348, and of each preceding Application in the chain including at least a Divisional application Ser. No. 11/998,951 and a Non-Provisional application Ser. No. 11/291,391, filed Dec. 1, 2005, which claims benefit under 35 U.S.C. §119(e) from prior U.S. Provisional Patent Application Ser. No. 60/633,046 filed on Dec. 2, 2004 entitled "An Illuminated Display System and Method of Use", by inventor Juan Enrique Cienfuegos, the entirety of disclosures of the above referenced Applications is hereby incorporated by reference as if fully set forth herein.

BACKGROUND OF THE INVENTION

1. Field of the Invention

The present invention generally relates to a networked triage system for placement on a user or receiving object. More particularly, but not by way of limitation, the present invention relates to a networked triage system and method for visually displaying information from a selection of light signals with programmable illuminated display systems whereby the information, for example, may be used for prioritizing the degree of medical care administered to a user.

2. Description of the Related Art

In the past, the concept of assessing an individual's medical condition and prioritizing that individual's need for medical care with respect to others requiring assistance is a concept commonly known as "Triage". Triage is one of the first applications of medical care applied to an individual and is often used as a technique to address the most seriously injured first. The triage concept is applied to humans and animals alike and in a variety of patient care settings including hospital emergency rooms, in the field with emergency medical service providers such as with natural disaster conditions and in battlefield settings. Illustratively, the triage concept is applied by the military, U.S. Homeland Security Agency, and the U.S. Federal Emergency Management Agency (FEMA).

Generally, triage techniques attempt to sort patients into categories for transport and immediate medical treatment. Triage is administered oftentimes in imperfect conditions where immediate medical care is limited, time is critical, and patients are prone to inaccurately advocating their precise medical condition.

Triage assessors generally tag patients according to the degree of injury. Many typical examples of triage tags are based on color coded information cards by which an assessor provides a written description of the patient's condition on that paper card.

Illustratively, in a battlefield setting, either a combat medic or corpsman provides triage assessments to injured soldiers on the battlefield. In practice, a medic is personally at risk from being fired on or the hazardous conditions associated with the battlefield. A medic's triage assessment must not only be accurate, but must be quickly provided so as not jeopardize the health of the injured soldier or of the medic themselves. Many times, a medic is not given the opportunity to provide a written description or even color code an injured soldier accordingly. Furthermore, battlefield conditions hinder one's ability to accurately read a corresponding triage card. Illustratively, smoke, dust, and changing weather conditions obscure one's ability to determine the triage status of an injured solider at a distance. Moreover, conditions such as complete darkness, underwater settings or in buried conditions could render the determination of written information on one's triage card as improbable. These difficulties are amplified when caring for several injured soldiers at the same time without a unified way to remotely prioritize injury. Unfortunately, there is no known device or method for quickly and accurately providing triage status at a distance in either day or night, such as status of an injured soldier in various battlefield settings.

Therefore, a need exists for a system and method for placement on a user that quickly and accurately provides information relating to the degree of injury of the user among at least one group of other users. There is also a need for a system and method for quickly and accurately providing information including triage information in varied visibility conditions and at a distance. Many other problems and disadvantages of the prior art will become apparent to one skilled in the art after comparing such prior art with the present invention as herein described.

SUMMARY OF THE INVENTION

Aspects of the invention are found in an interface module for a display interface of an illuminated display system that includes an operating subframe and a selector coupled to the operating subframe. The operating subframe is further coupled to a plurality of light emitters. Each light emitter provides a different predetermined wavelength of light than the other light emitters from the plurality of light emitters. Each respective predetermined wavelength provides information relating to a corresponding predetermined status of a user. Each desired light emitter is chosen, by the selector for illumination, from the plurality of light emitters according to a lighting operation sequence. The operating subframe includes a module processor coupled to the plurality of light emitters and the selector, a removable external memory device, and an external memory processor, and a bus coupled to the module processor and the removable external memory processor. The module processor stores illuminated light emitter information in a computer readable format within the removable external memory device. In one aspect, an operation method for an operating subframe of an illuminated display system is provided.

In one further aspect, the operating subframe features a plurality of external sensors and a mote module coupled to the plurality of external sensors and the module processor. In operation, the mote module creates mote sensor data from the plurality of external sensors whereas the module processor combines illuminated light emitter data with mote sensor data from the mote module to create an identification signal for transmission from the illuminated display system.

Other aspects, advantages, and novel features of the present invention will become apparent from the detailed description of the present invention when considered in conjunction with the accompanying drawings.

BRIEF DESCRIPTION OF THE DRAWINGS

The present invention is illustrated by way of example and not by limitation in the accompanying figures, in which like references indicate similar elements, and in which:

FIG. 3 are orthographic views from the top illustrating one exemplary embodiment of an illuminated display system, in particular.

FIG. 4 are orthographic views illustrating one exemplary embodiment of an illuminated display system, in particular.

FIG. 5 are orthographic views illustrating one exemplary embodiment of an illuminated display system, in particular.

FIG. 6 illustrate isometric views of an illuminated display system, in particular, FIG. 6a shows an isometric view illustrating a power source stowed in a base body, FIG. 6b is an isometric view illustrating one exemplary embodiment of a second portion of a base body, and FIG. 6c is an orthographic view illustrating one exemplary embodiment of a second portion of a base body;

FIG. 7 are exploded orthographic views of an illuminated display system, in particular, FIG. 7a illustrates an interface module coupled with a chamber support for receiving a power source and an electronic identification tag, FIG. 7b illustrates an second portion including a sensor assembly, FIG. 7c illustrates a base body that forms an interference fit with an attachment flange, and FIG. 7d illustrates a second portion defining a storage chamber;

FIG. 8 generally illustrate various embodiments of the interface module, in particular.

Skilled artisans appreciate that elements in the Figures are illustrated for simplicity and clarity and have not necessarily been drawn to scale. For example, the dimensions of some of the elements in the Figures may be exaggerated relative to the other elements to help improve understanding of the embodiments of the present invention.

DETAILED DESCRIPTION

For a more complete understanding of the present invention, preferred embodiments of the present invention are illustrated in the Figures. Like numerals being used to refer to like and corresponding parts of the various accompanying drawings. It is to be understood that the disclosed embodiments are merely exemplary of the invention, which may be embodied in various forms.

FIGS. 1-8 generally illustrate one aspect, among others, of an illuminated display system 5 of a plurality of illuminated display systems 101 within a networked triage system 100. Each illuminated display system 5 is typically placed on a user or receiving object. Generally, an illuminated display system provides information associated with the user or receiving object through light emission at various wavelengths. In this application, the terms "user" and "receiving element" respectively refer to a living being and non-living object by which an illuminated display system is attached to. For example, an illuminated display system provides information relating to the injury of a user in a triage situation such as the degree of injury, the nature of injury, and likelihood of survival. Moreover, in this application, the term "light" refers to the entire electromagnetic spectrum of light including infrared light whereas the term "visible light" refers to a wavelength range of the electromagnetic spectrum that is observable to the human eye. Each respective predetermined wavelength of light provides information relating to a user's status, such as information relating to the degree of injury of the user in a triage setting.

Specifically as viewed in FIGS. 1-3, 4a, 7a, and 8, the illuminated display system 5 includes a plurality of light emitters 22. At least one light emitter from the plurality of light emitters 22 is selected for illumination thereof according to the injury of the user. The illuminated display system 5 may then be attached to the user or receiving object while operatively illuminated. Illumination of a desired light emitter provides information describing the current status of the user, such as, among others, the kind of injury received, the likelihood for injury recovery or the location of the injured party, survival status of the user, and state of contamination of the user.

Figure 1:
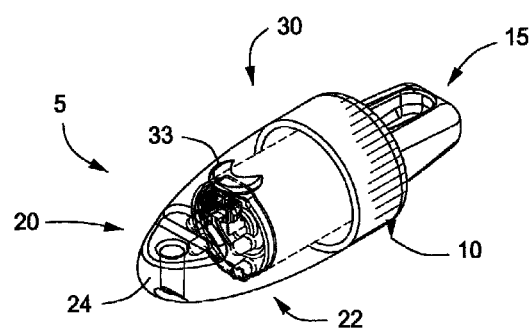
FIG. 1 is an isometric view from the top illustrating an illuminated display system for placement on an user according to the present invention, the illuminated display system includes a plurality of light emitters that individually emit a predetermined wavelength band relating to the user's status.
Figure 2:
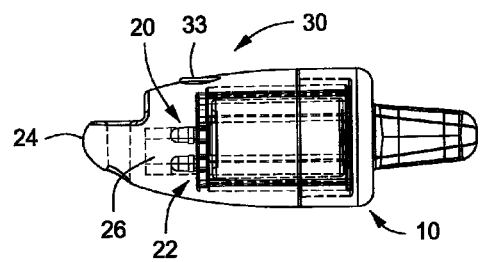
FIG. 2 is an orthographic view from the side illustrating one exemplary embodiment of an illuminated display system.
Figure 3A:
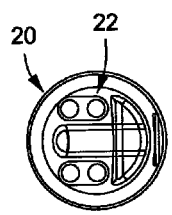
FIG. 3a is an orthographic view from the front illustrating a display interface of the illuminated display system.
Figure 3B:
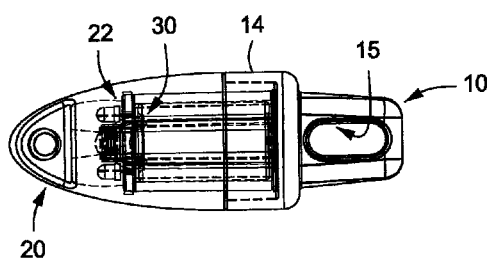
FIG. 3b is an orthographic view from the top illustrating an illuminated display system having a fastening interface.

Referring to FIG. 1, the illuminated display system 5 includes a base assembly 10. The base assembly 10 includes a display interface 20. In one exemplary embodiment, the display interface 20 is coupled to the base assembly 10. As shown in FIG. 1, the plurality of light emitters 22 are incorporated with the display interface 20.

The illuminated display system 5 includes a dial assembly 30. The dial assembly 30 is operatively coupled to the base assembly 10.

The illuminated display system 5 further includes a selector 33. As shown in the embodiment of FIG. 1, the selector 33 is disposed on the dial assembly 30. Operatively, according to a lighting program sequence as discussed below, the selector 33 applies a voltage to a desired light emitter from the plurality of light emitters 22 for illumination thereof. Thus, according to a lighting program sequence the selector 33 either engages or disengages a desired light emitter from the plurality of light emitters. In one exemplary embodiment, the illuminated display system 5 is rendered in a consistent, electrically "off" position until the selector 33 engages with a light emitter from the plurality of light emitters 22. In this manner, the illuminated display system 5 will be illuminated as desired.

Moreover, in one exemplary embodiment, the dial assembly 30 further includes an interface module 40. Referring to FIGS. 7 and 8, the interface module 40 includes a module processor 65, a memory unit 64a, and at least one programming interface 67 coupled to the module processor 65. In one exemplary embodiment, the module processor 65 receives a voltage from the selector 33 indicating the desired light emitter for illumination thereof and stores corresponding last lit information in the memory unit 64a. Upon reestablishment of power to the interface module 40, the last lit information is retrieved from the memory unit 64a to re-illuminate the desired light emitter via the module processor 65. Accordingly, due to storage of last lit information in the memory unit 64a, triage status information of the injured user as indicated by the desired illuminated light emitter is maintained despite power loss to the illuminated display system 5.

Figure 11:
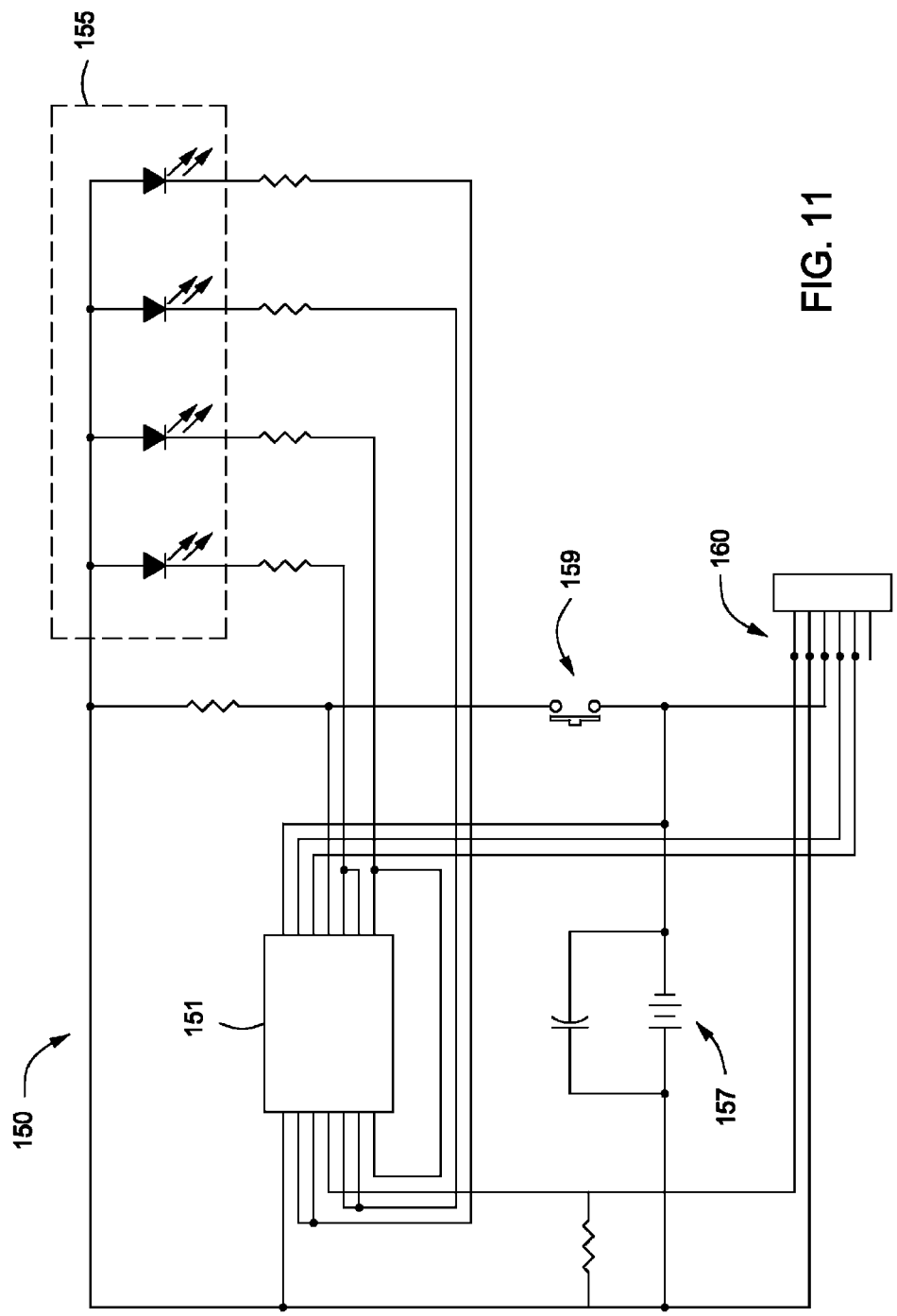
FIG. 11 is a circuit diagram illustrating one exemplary embodiment of an illuminated display system.

Illustratively, FIG. 11 is a circuit diagram showing one exemplary embodiment of an illuminated display system 150. Similar to that described above, the illuminated display system 150 includes a module processor 151 and a power source 157 coupled to the module processor. Moreover, a plurality of light emitters 155 is coupled to the module processor 151 and is activated by a selector 159. The illuminated display system 150 further includes a programming interface 160 coupled to the plurality of light emitters 155.

Each light emitter from the plurality of light emitters 22 radiates a different wavelength of light than other light emitters from the plurality of light emitters 22. In this manner, each respective predetermined wavelength of light provides information associated with the status of a user or receiving object. For example, each light emitter provides correspondingly different information from the other emitters as related to the degree of injury of an injured user, such as a soldier. Those of ordinary skill in the art will readily recognize that each respective predetermined wavelength represents corresponding predetermined information to be conveyed about the user. Each light emitter is selected from the plurality of light emitters according to a lighting operation sequence stored in the memory unit 64a. Ultimately, as a desired light emitter is selectively illuminated, the illuminated display system 5 when placed on an injured user facilitates quick, efficient prioritization of the injured user for future treatment and transport in a triage setting as well as a search and rescue setting, among others.

In one exemplary embodiment, an illustrative lighting operation sequence among others is described as follows. After making a brief clinical assessment of an injured user, a light emitter exhibiting a distinct wavelength is illuminated to indicate the degree of injury according to a predetermined assignment of triage wavelength bands for illumination. With the illustrative lighting operation sequence, a selector is pressed once to access infrared light, and pressed twice to obtain blinking infrared light. The selector is pressed a third time for red light, a fourth time for green light, a fifth time for blue light, and a sixth time to end the lighting operation sequence. The lighting operation sequence may then be restarted in the manner described above. With another illustrative lighting operation sequence, a selector is pressed once to access red light, and pressed twice to obtain amber or yellow light. The selector is pressed a third time for green light, a fourth time for blue light, and a fifth time to end the lighting operation sequence. The lighting operation sequence may then be restarted in the manner described above. Those of ordinary skill in the art will readily recognize that the lighting operation sequence may include any combination of continuous, alternating or intermittently illuminated light emissions at various wavelengths. For example, each of light emitters from the plurality of light emitters will all illuminate for intermittent periods according to one embodiment of a lighting operation sequence whereas each of the light emitters from the plurality of light emitters will sequentially alternate illumination according to another embodiment of a lighting operation sequence.

Figure 8B:
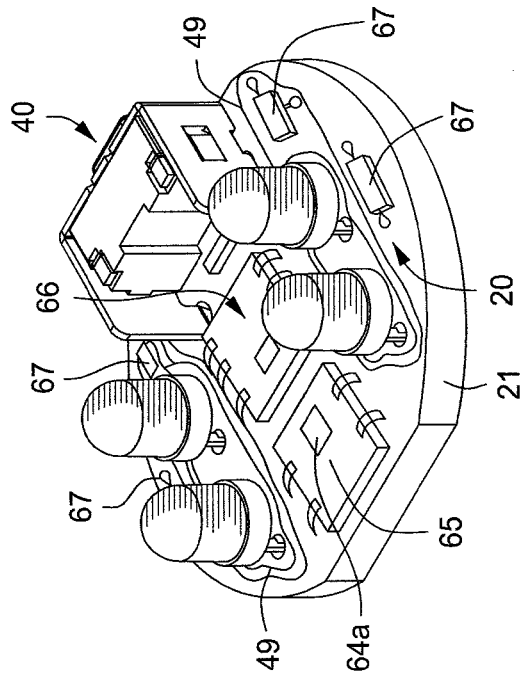
FIG. 8b illustrates an isometric view of an interface module including an id tag processor.
Figure 8A:
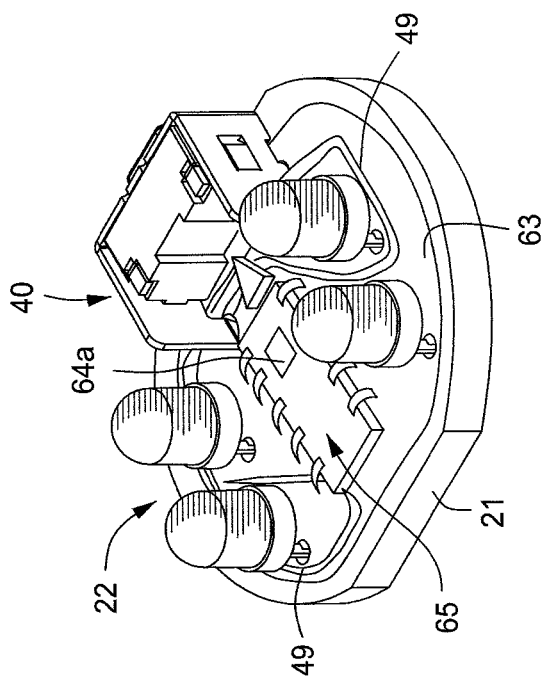
FIG. 8a illustrates an isometric view of an interface module including a module processor.
Figure 8C:
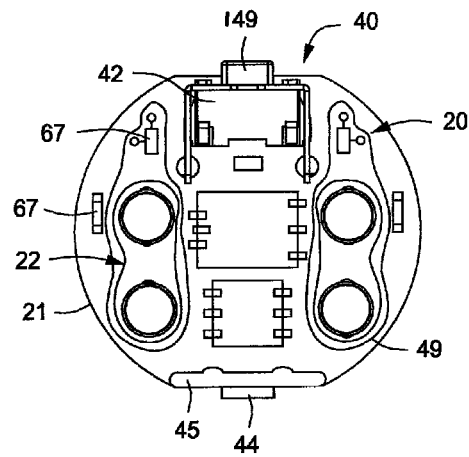
FIG. 8c illustrates an isometric view of an interface module including programming pads.
Figure 8D:
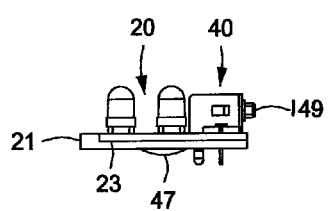
FIG. 8d is an orthographic view from the side of a display interface.
Figure 8E:
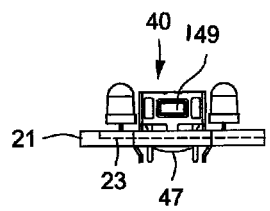
FIG. 8e is an orthographic view from the side illustrating a display interface.

In operation, as shown in FIGS. 8c, d, and e, as the selector 33 is pressed the interface module 40 receives a compressive force as applied to a mode activation interface 49. Accordingly, the physical input applied by the selector 33 on the mode activation interface 49 is converted to an electrical signal output by the selector unit 42 coupled to the mode activation interface 49. The resulting electrical signals are then received and manipulated by a module processor 65 provided by the interface module 40. Based on the lighting operation sequence, the module processor 65 facilitates the activation of a desired light emitter from the plurality of light emitters 22. In one exemplary embodiment, information associated with the activation of the desired light emitter is stored in a memory unit 64a coupled to the module processor 65.

In one exemplary embodiment, the plurality of light emitters 22 includes a light emitting diode for emitting light at various wavelengths along the entire electromagnetic spectrum. In particular, the plurality of light emitters 22 includes a light emitting diode for providing an infrared wavelength band of light. Illustratively, a light emitting diode provides infrared light in 800 nanometer (nm), 820 nm, 830 nm, 880 nm, 940 nm, and 950 nm wavelengths. The plurality of light emitters 22 includes a light emitting diode for providing a wavelength band of white light. The plurality of light emitters 22 includes a light emitting diode for radiating a wavelength band of amber visible light. The plurality of light emitters 22 includes a light emitting diode for radiating a wavelength band of red visible light. The plurality of light emitters 22 includes a light emitting diode for supplying a green wavelength band of visible light. The plurality of light emitters 22 further includes a light emitting diode for generating a blue wavelength band of visible light. The plurality of light emitters 22 includes a light emitting diode for supplying an ultraviolet wavelength band of visible light. In one exemplary embodiment, the plurality of light emitters 22 may include an single light emitting diode arranged on the display interface 20 for providing blue, yellow, green, red, and purple visible light in addition to an infrared band, an intermittent band, and alternating bands of infrared light.

Those of ordinary skill in the art will readily recognize other widely known light emitters for selective illumination about the display interface 20 that emit light at a wide band of various wavelengths. Illustratively, in one exemplary embodiment, the plurality of light emitters 22 includes inorganic light emitting diodes. In one exemplary embodiment, the plurality of light emitters 22 includes organic light emitting diodes. In one exemplary embodiment, the plurality of light emitters 22 includes a combination of inorganic and organic light emitting diodes. In one exemplary embodiment, the plurality of light emitters 22 may include an incandescent light emitter. In one exemplary embodiment, the plurality of light emitters 22 includes a plasma light emitter, such as, among others, a fluorescent light and a mercury vapor light. In one exemplary embodiment, the plurality of light emitters 22 may include electroluminescent light. In one exemplary embodiment, the plurality of light emitters 22 includes a LASER light. In one exemplary embodiment, the plurality of light emitters 22 includes a Liquid Crystal Display, LCD, light emitter.

In one exemplary embodiment, to amend in part or supersede the lighting operation sequence, the at least one programming interface 67 receives a command sequence. Illustratively, in one exemplary embodiment, the at least one programming interface 67 comprises a plurality of program pads for a peripheral interface controller processor that receive a command sequence from a programming device such as, among others, an In-Circuit Programmer and an In-Circuit Debugger (ICD). In this manner, a portable programming device can be taken anywhere to either amend or entirely supersede the lighting operation sequence.

On its receipt, the command sequence integrates with the lighting operation sequence via the module processor 65 to thus define a reprogrammed lighting sequence. In one exemplary embodiment, the reprogrammed lighting sequence is stored in memory via the module processor 65. As such, each light emitter is selected from the plurality of light emitters 22 according to the reprogrammed lighting operation sequence. In effect, the reprogrammed lighting operation sequence becomes the new lighting operation sequence for storage in the memory unit 64a and for future execution by the illuminated display system 5.

Shown in FIG. 4-7, each illuminated display 5 for illustrative purposes is generally divided as the base assembly 10 positioned on one side of the interface module 40 and the dial assembly 30 positioned on another side of the interface module 40. As such, the base assembly 10 includes a base body 14 whereas the dial assembly 30 includes a display body 6. In one exemplary embodiment a combination of the base body 14 and the display body 6 may be composed of a transparent material. In one exemplary embodiment a combination of the base body 14 and the display body 6 may be composed of a translucent material. In one exemplary embodiment a combination of the base body 14 and the display body 6 may be composed of an opaque material. In one exemplary embodiment, a combination of the base body 14 and the display body 6 may be composed of a semi-resilient material, such as silicone. In one exemplary embodiment, a combination of the base body 14 and the display body 6 may be composed of a water proof material.

Figure 4A:
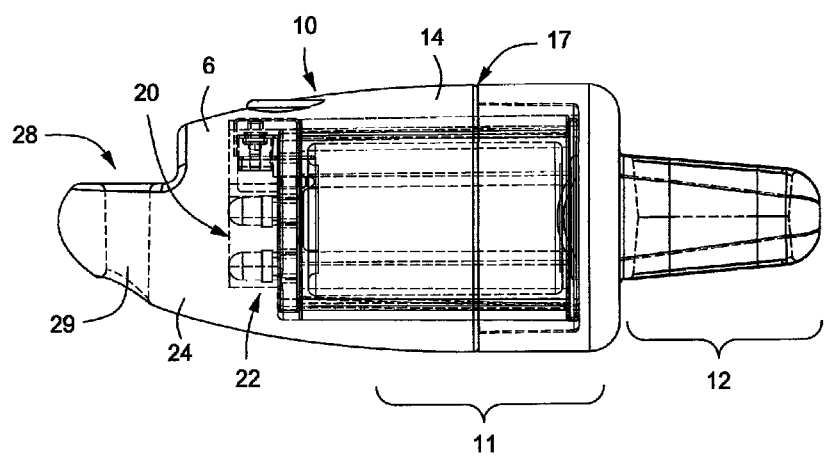
FIG. 4a shows an illuminated display system having a first portion and a second portion.
Figure 4B:
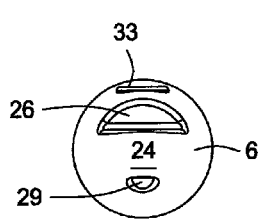
FIG. 4b shows an orthographic view from the front illustrating an optical modifier.
Figure 4C:
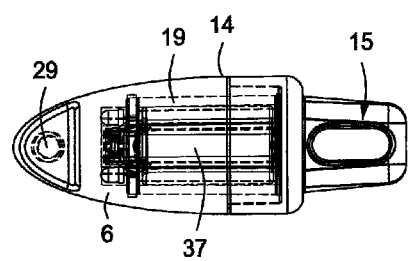
FIG. 4c shows an orthographic view from the top illustrating a power source positioned within a display system body.
Figure 5A:
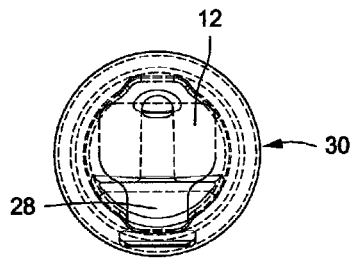
FIG. 5a shows the illuminated display system from the back.
Figure 5B:
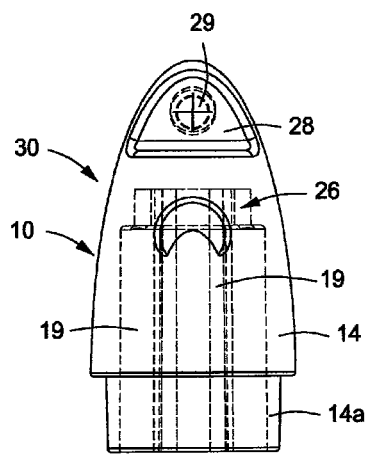
FIG. 5b shows the illuminated display system illustrating a base body having an attachment flange.
Figure 5C:
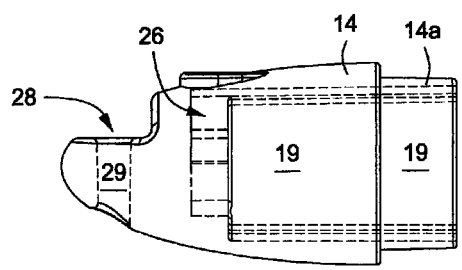
FIG. 5c shows an illuminated display system having an alignment element.

Specifically referring to FIG. 4a, in one exemplary embodiment, the base body 14 includes a first portion 11 and a second portion 12 extending outwardly from the first portion 11. FIGS. 7b-7d illustrate various embodiments for the second portion 12. In FIG. 7b, the second portion 12 comprises a resilient member for applying a compressive force against an in injured user. As shown, the embodiment of FIG. 7b includes a sensor assembly 57. Illustratively, the sensor assembly 57 includes an electrode 58 and an adhesive laminate 59 disposed on the resilient member and adjacent to the electrode 58 to facilitate continuous contact against the injured user. In one exemplary embodiment, the electrode 58 comprises a heart monitor. In FIG. 7d, the second portion 12 defines a storage chamber 56 for holding a variety of objects.

The storage chamber is configured to accommodate a wide range of useful items such as additional power sources such as batteries, electronic identification tags, radio frequency (RF) identification microprocessors, biomedical sensors like heart-rate sensors and other well known sensors, global positioning system (GPS) locators and other well known locators, memory storage devices, and emitters/receivers. Moreover, as shown in FIG. 7d, the second portion may define a fastening interface 15 for receiving a fastening means of a type well known in the industry to secure the illuminated display system 5 to an injured user or object In FIGS. 4a, 5c, and 7, the base body 14 defines a receiving chamber 19. The receiving chamber 19 is configured to accommodate a wide range of useful items such as power sources such as batteries, electronic identification tags, radio frequency (RF) identification microprocessors, biomedical sensors like heart-rate sensors and other well known sensors, global positioning system (GPS) locators and other well known locators, memory storage devices, and emitter/receivers. Operatively, in one exemplary embodiment, the receiving chamber 19 contains at least one battery for powering the interface module 40 including a desired light emitter from the plurality of light emitters 22. In one exemplary embodiment, the at least one battery comprises a lithium ion battery.

Figure 8F:
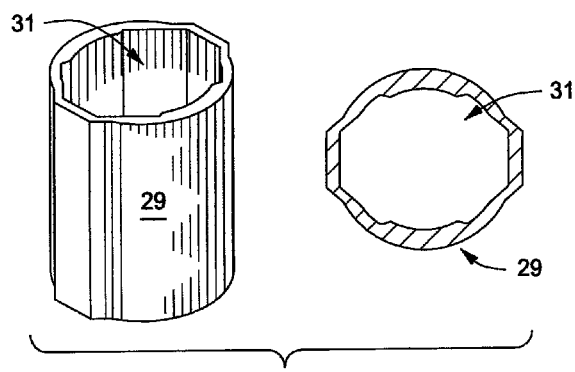
FIG. 8f illustrates a chamber support.

Shown in FIGS. 7a and 8f, a chamber support 29 is optionally disposed along the periphery of the receiving chamber 19 to structurally support the receiving chamber 19. Accordingly, the chamber support is composed of either a semi-rigid or rigid material. In operation, in one exemplary embodiment, the chamber support 29 comprises a tube having a support passageway 31 for receiving at least one battery therein while the outer surface of the chamber support 29 abuts along the periphery of the receiving chamber 19.

Referring to FIGS. 6a, 7a, c, and 8c at least one binder element 44 is provided for mechanically securing the power source to the interface module 40. The at least one binder element 44 is composed of either a semi-rigid or rigid material, such as an electrically conducive metal, metal alloy, or electrically conductive ceramic. Shown in FIGS. 8c and 9a, the at least one binder element 44 includes a module support for coupling to the interface module 40 at one end and extends the length of the receiving chamber and thus power source therein, and includes a contact support holder for coupling to a contact support 43 at another end. The at least one binder element 44 mechanically fastens the interface module 40 adjacent to the power source 62, such as among others a battery, and, in one illustration, electrically positions the battery's electrical terminals with the interface module 40 to supply power thereto. Electrically, in the illustration, the at least one binder element 44 establishes an electrical contact between the two electrical terminals of the at least one battery to complete a circuit for providing electrical power to the interface module 40. Those of ordinary skill in the art will readily recognize that, addition to the receiving chamber 19, the configuration of the at least one binder element 44, power source 62, and the contact support 43 may be reproduced within the storage chamber 56 of the second portion 12 to provide at least one additional power supply for powering the interface module 40.

Moreover, as shown in FIG. 6a, the contact support 43 is positioned against the electrical terminal of the battery 62 as the contact support 43 secured to the contact support holder 44b. In the illustration, the contact support 43 includes a resilient element 43a to dampen mechanical shock forces applied to the at least one battery 62 within the receiving chamber 19. The contact support 43 in FIG. 6a is rendered to slide along or away from the contact support holder 44b to gain full access to the battery in the receiving chamber 19 so as to interchange an expended battery for a fully charged battery.

FIGS. 4a and 7c, illustrate an opening accessway 17. In one exemplary embodiment, the base body 14 defines the opening accessway 17. Operationally, in one exemplary embodiment, at least one portion of the illuminated display system 5 may be pulled apart from another portion of the illuminated display systems to gain access to the interface module 40, the receiving chamber 19, and the storage chamber 56 therein.

As illustrated in FIGS. 7*a* and *c*, in one exemplary embodiment, the base body 14 is configured to establish an interference fit at the opening accessway 17. Operatively, the base body 14 is pulled apart at the opening accessway 17 to expose the receiving chamber therein 19.

In particular, as shown in FIG. 7*a*, the base body 14 defines an attachment flange 14*a* at one end of the illuminated display system 5 so that the base body 14 of FIG. 7*c* is positioned over the attachment flange 14*a* to establish an interference fit. The base body 14 of FIG. 7*c* is pulled along the attachment flange 14*a* toward the interface module 40 to terminate at and thus define the opening accessway 17.

Referring to FIGS. 7 and 8, the illuminated display system 5 may further include an id tag processor 66. The id tag processor 66 may comprise a processor of a type well known in the industry such as a Radio Frequency Identification, RFID, processor.

As shown in FIGS. 8*b* and 8*c*, in one exemplary embodiment, the id tag processor 66 is coupled to the module processor 64, the memory unit 64*a*, and the power source 62. In one exemplary embodiment, as shown in FIG. 8*c*, the id tag processor 66 is coupled to an antenna array 49 for emitting and receiving signals in cooperation with the id tag processor 66. Illustratively, in one exemplary embodiment, the id tag processor 66 as coupled to the module processor 65, the memory unit 64*a*, and the power source 62 to collectively define an ultra high frequency active RFID tag. Optionally, as shown, the antenna array 49 is integral with a module substrate 21 of the interface module 40.

Those of ordinary skill in the art will readily recognize those configurations utilizing an id tag processor for facilitating identification signal emissions such as providing self-sustaining electronic identification tags for operative integration with the illuminated display system 5. In one exemplary embodiment, an id tag processor from a self-sustaining identification tag of a standard type well known in the industry integrates with a module processor from the illuminated display system to facilitate the generation of an identification signal as discussed below.

In one exemplary embodiment, an id tag processor from an illuminated display system receives identifier information from an external source electronic identification tag such as a military radio frequency identification (RFID) or "dog" tag or electronic emissions from other sources such as from rescue or medical equipment. Accordingly, the id tag processor incorporates this information into a resulting identification signal for emission from the illuminated display system.

The id tag processor 66 generates an identification signal. In one exemplary embodiment, the identification signal includes identifier information unique to the id tag processor 66. In one exemplary embodiment, the identification signal includes personal information regarding the injured user associated with the illuminated display system 5. Illustratively, for example, personal information may include among others military dog tag information of: nationality, name, rank, serial number, religion, and detailed accounting of injury. The personal information is stored in the memory unit 64*a* and incorporated within the identification signal via either combination of the module processor 65 or the id tag processor 66.

In one exemplary embodiment, the id tag processor 66 and the module processor 65 cooperatively generate an identification signal. Accordingly, the identification signal includes identifier information and light emitter wavelength information. Illustratively, the identifier information includes, among other information, information unique to the particular id tag processor 66, information associated with the degree of injury, and personal information of the injured user.

In one exemplary embodiment, the identification signal includes last lit information regarding the illumination of a desired light emitter either before transmission from the illuminated display system 5 or on power loss of the illuminated display system 5. Accordingly, the degree of injury and triage status of the injured user is determined from the identification signal indicating the last active light emitter from the plurality of light emitters 22 of the illuminated display system 5.

Alternatively, in one exemplary embodiment as shown in FIGS. 7*d* and 8*a*, the illuminated display system 5 includes an electronic identification tag 63. In one exemplary embodiment, the electronic identification tag 63 is of a standard type well known in the industry such as, among others, an ultra high frequency active RFID tag, a battery assisted passive RFID tag and an ultra high frequency passive RFID tag.

Accordingly, the electronic identification tag 63 couples to the interface module 40 and generates an identification signal. In one exemplary embodiment, the electronic identification tag 63 is a self sustaining module that is provided by the networked triage system. The electronic identification tag 63 sends and receives identification signals associated with the illuminated display system 5.

Accordingly, the identification signal includes identifier information and light emitter wavelength information. Illustratively, the identifier information includes, among other information, information unique to the particular electronic identification tag 63, information associated with the degree of injury, and personal information of the injured user. In one exemplary embodiment, as discussed below, identifier information at least in part comes from an external source electronic identification tag hereinafter defined in this disclosure as an RFID tag that is not necessarily used for triage. Illustratively, examples of an external source identification tag include a military "dog" tag, a passport, a drivers license, and a credit card.

In one exemplary embodiment, the identification signal includes personal information regarding the injured user associated with the illuminated display system 5. Illustratively, for example, personal information may include among others military dog tag information of: nationality; name; rank; serial number; religion; previous injuries; medical conditions as well as known allergic reactions; and detailed accounting of injury.

As stated above, each illuminated display system further includes a dial assembly. The dial assembly includes an interface module and a selector coupled to the interface module. The interface module includes a module processor, a memory unit, and at least one programming interface coupled to the module processor. The memory unit stores the lighting operation sequence.

Each illuminated display system further includes an id tag processor. Accordingly, each illuminated display system emits an identification signal via the id tag processor. A portable network device receives the identification signal.

In one exemplary embodiment, a portable network interface establishes a local area network (LAN) or "user group" for monitoring and assigning triage status to each injured user with a corresponding illuminated display system. Illustratively, the portable network interface enables a relief provider such as a combat medic to compile and access information received from a plurality of illuminated display systems where each illuminated display system is coupled to an injured user such as a soldier near the portable network interface.

Similar to the above described, each illuminated display system couples to an injured user. Each illuminated display system includes a plurality of light emitters. Each light emitter supplies a predetermined wavelength of light providing information relating to a corresponding predetermined status of the user. Each light emitter is selected from the plurality of light emitters according to a lighting operation sequence.

Illustratively, in one exemplary embodiment, an injured user includes an electronic identification tag comprising a military dog tag of a type well known in the industry. The military dog tag emits an identification signal including personal information associated with the injured user. The identification signal is received by an id tag processor of the illuminated display system. Accordingly, a combat medic is able to position the illuminated display system adjacent to a standard military issue dog tag and retrieve information therefrom via the id tag processor. The personal information from the identification signal is stored in a memory unit a coupled to the id tag processor. The personal information integrates with an identification signal via the module processor that is coupled to the memory unit. In one exemplary embodiment, information regarding the status of the corresponding illuminated light emitter from the plurality of light emitters provided by the respective illuminated display system stored in the memory unit integrates with the identification signal via the module processor. Optionally, as discussed in detail below, a sensor signal integrates within the identification signal via a module processor from an illuminated display system. The module processor is coupled to the id tag processor, and a sensor assembly. Illustratively, the sensor assembly is coupled to the injured user to measure heart rate. Thus, ultimately, the identification signal for the corresponding illuminated display system is sent to a portable network interface.

Figure 9:
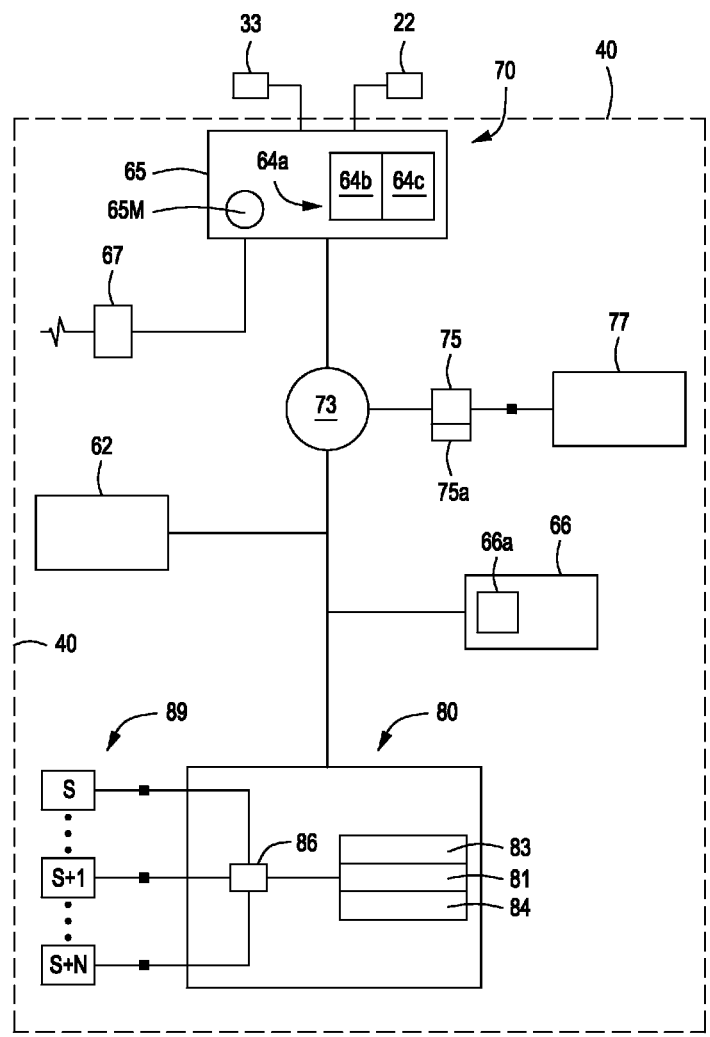
FIG. 9 is a schematic electrical block diagram illustrating one embodiment of an operating subframe for the interface module, the operating subframe effectuates the electrical operations of the interface module.

Referring now to FIG. 9, one embodiment of an operating subframe 70 is shown. Accordingly, for the embodiment of FIG. 9, the operating subframe 70 facilitates electrical operations of the interface module 40 including all software, logical, and hardware operations thereof.

For the embodiment of FIG. 9, the interface module 40 of the display interface 20 for the illuminated display system 5 includes an operating subframe 70 and the selector 33 coupled to the operating subframe 70. The operating subframe 70 is further coupled to the plurality of light emitters 22. As shown, the plurality of light emitters 22 is provided by the display interface 40.

Similar to the above description, each light emitter provides a different predetermined wavelength of light than the other light emitters from the plurality of light emitters 22. Each respective predetermined wavelength provides information relating to a corresponding predetermined status of the user. In battlefield triage, one exemplary predetermined status of an injured user may be understood as red for "immediate" attention, yellow for "delayed" attention, green for "minimal" attention and blue for "expectant" status.

Each desired light emitter is chosen, by the selector 33 for illumination, from the plurality of light emitters according to a lighting operation sequence. With one illustrative lighting operation sequence, a selector is pressed once to access infrared light, and pressed twice to obtain blinking infrared light. The selector is pressed a third time for red light, a fourth time for green light, a fifth time for blue light, and a sixth time to end the lighting operation sequence.

As shown in FIG. 9, the operating subframe 70 includes a module processor 65. The module processor 65 is coupled to the selector 33 and the plurality of light emitters 22. Those of ordinary skill in the art will readily recognize that the module processor 65 comprises a processor of a type well known in the industry suitable for executing the operations of the illuminated display system 5. In one exemplary embodiment, the module processor 65 comprises microcontroller, such as a PIC16F636 microcontroller.

The module processor 65 in one embodiment is coupled to a bus 73. The bus 73 features chip select function. In one embodiment of the operating subframe 70, the chip select function is applied to the module processor 65 to designate the module processor 65 as the master chipset such that all other processors provided by the operating subframe 70 are responsive to the module processor 65.

Operatively, the bus 73 permits the module processor 65 to interface with various hardware and functional components of the operating subframe 70 for control thereof. In one embodiment, the bus 73 comprises a serial port interface (SPI) bus of a type well known in the industry.

The bus 73 is coupled to the power source 62 for the illuminated display system 5. Accordingly, the operating subframe 70 receives power from the power source 62 to facilitate operation of the illuminated display system 5.

The module processor 65 is coupled to at least one programming interface 67. In the same manner discussed above, the at least one programming interface 67 receives a command sequence.

Illustratively, in one exemplary embodiment, the at least one programming interface 67 comprises a plurality of program pads for a peripheral interface controller processor that receive a command sequence from a programming device such as, among others, an In-Circuit Programmer and an In-Circuit Debugger (ICD). In this manner, the programming interface provides at least one reprogrammed lighting operation sequence to the plurality of light emitters 22 via the module processor 65. A portable programming device can thus be taken anywhere to either amend or entirely supersede the lighting operation sequence for the illuminated display system.

The module processor 65 is further coupled to a memory unit 64a. In one embodiment, the module processor 65 comprises a microcontroller such that the memory unit 64a is integral with the microcontroller. Accordingly, as illustrated in FIG. 9, the memory unit 64a includes a RAM memory unit 64b as the operative core memory for the microcontroller and includes a ROM memory unit 64c for storing the lighting operating sequence and commands received via the programming interface 67.

The operating subframe 70 further includes an external memory processor 75 and a removable external memory device 77. Shown in FIG. 9, the external memory processor 75 is coupled to the bus 73. As such, the external memory processor 75 functions as a slave chipset to that of the module processor 65. Thus, in operation, the external memory processor 75 facilitates reading and writing of data to the removable external memory device 77 as dictated by the module processor 65. The module processor 65 stores illuminated light emitter information in a computer readable format within the removable external memory device 77.

In one embodiment, among others, the removable external memory device 77 comprises a flash memory device. The flash memory device is of a type well known in the industry such as memory card that can be removed from the illuminated display system 5 or an EEPROM device.

Illustratively, in one embodiment, the triage status of the injured user is continuously updated with the illuminated display system 5 and, optionally, with a portable network interface as described above such that the updates are saved external memory device 77 of the operating subframe 70 as the injured user is brought from the mass casualty site, along a designated rescue evacuation route, and to a final destination for receiving care. Accordingly, at the final destination for receiving care, the illuminated display system accurately reflects the current status of the injured user as the updated triage status is stored in the external memory device, accessed via the module processor 65, and sent from the illuminated display system as an identification signal and as displayed by a corresponding illuminated light emitter or similar illuminated device at the final destination for receiving care.

Optionally, as shown in the embodiment of FIG. 9, the external memory processor 75 further includes an external transceiver 75*a* for wirelessly sending data from the illuminated display system as an identification signal thus illuminated light emitter information as well as identification information, among others, could be retrieved by a receiving device at the final destination. In one embodiment, the external memory processor 75 is wirelessly coupled to the removable external memory device 77 via the external transceiver 75*a*. In one embodiment, the external transceiver 75*a* comprises a BLUETOOTH transceiver.

Moreover, as shown, the module processor 65 may further include a microphone 65M that may be operated by a first responder depressing the selector 33 to record audio data, such as the verbal status of the injured user assigned to the illuminated display system 5, to the memory unit 64*a* or removable external memory device 77. Thus, along with the illuminated display system 5, personnel at the final destination may obtain recorded audio information regarding the injured user via the module processor 65.

In one embodiment, the operating subframe 70 includes an id tag processor 66. The id tag processor 66 is coupled the module processor 65 via the bus 73. The id tag processor 65 includes a radio frequency (rf) id tag processor, a transceiver for accommodating rf signals, and a tag memory unit 66*a*. In one embodiment, the id tag processor 65 comprises a microcontroller.

In operation, a combat medic is able to position the illuminated display system 5 adjacent to a standard military issue dog tag, which is typically an rf id emitter, and retrieve information therefrom via the id tag processor 65. The combat medic is also able to illuminate a light emitter from the illuminated display system 5 according to the triage status of the injured user as well as capture the identifier information associated with the user also with the illuminated display system 5 as well via the id tag processor 65. In addition to illuminated light emitter information, audio files, and sensor information, the module processor 65 stores identifier information and other information from the id tag processor 65 all within a computer readable format in the removable external memory device 77

The module processor 65 combines illuminated light emitter data with identifier information from the id tag processor 66 to create an identification signal for transmission from the illuminated display system 5, via the external transceiver 75*a* or other well known device in the industry. In one exemplary embodiment, the id tag processor 66 and the module processor 65 independently emit an identification signal and a predetermined wavelength of light via a designated light emitter to, respectively, provide information relating to a corresponding predetermined status of the injured user. Moreover, the module processor 65 and the id tag processor 66 cooperatively work to generate the identification signal to include both identifier information and light emitter wavelength information. In one exemplary embodiment, light emitter wavelength information includes information associated with which light emitter from the plurality of light emitters is illuminated to indicate the predetermined status of the user.

Further referring to FIG. 9, the operating subframe 70 includes a mote module 80. The mote module 80 is coupled to the module processor 65, the removable external memory device 77, the power source 62, and the programming interface 67 via the bus 73.

The mote module 80 includes a mote processor 81. The mote processor 81 facilitates transfer of mote sensor data from the mote module 80 to various components of the operating subframe 70 such as the module processor 65, the removable external memory device 77, and the programming interface 67. In one exemplary embodiment, the mote module 80 comprises a microcontroller, such as the ADVANTIC CM5000 or any well known wireless sensor node based on the "Berkeley board, TelosB" mote platform. As shown in FIG. 9, the mote module 80 is coupled to the removable external memory device 77 such that the mote module 80 stores mote sensor data to the removable external memory device 77.

The mote module 80 further includes a plurality of external sensors 89 coupled to the mote processor 81. The plurality of external sensors 89 provide mote sensor data to the mote processor 81. In one exemplary embodiment, at least one of the external sensors of the plurality of external sensors 89 comprises a dosimeter for detecting radioactive exposure of the user by which the illuminated display system 5 is assigned to. Such dosimeter may optionally feature wireless capability and further include a wireless gamma ray and/or neutron detector. Further examples, among others, of external sensors include HazMat detectors, chemical warfare agent detectors, hazardous gas detection systems, air sample detectors, and biological warfare agent detectors.

Figure 9A:
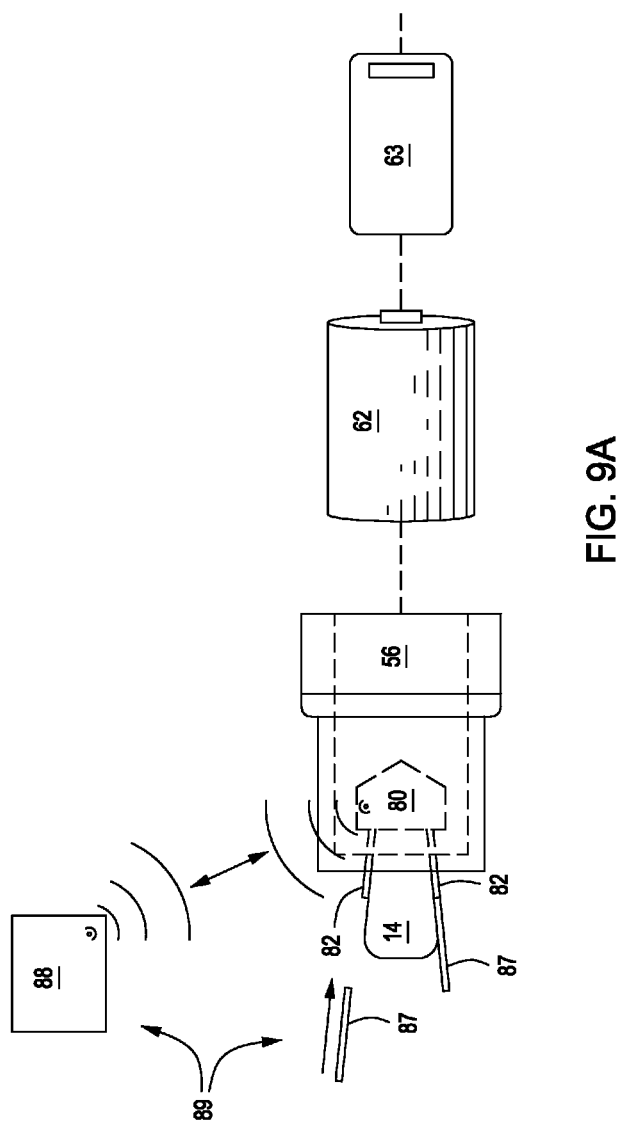
FIG. 9a is a schematic diagram of one embodiment of an illuminated display system illustrating a mote module of the operating subframe coupled to a plurality of external sensors, through wireless or hardware means.

The mote module 80 includes a transceiver 83 coupled to the mote processor 81. Operatively, in one exemplary embodiment, the transceiver 83 facilitates the wireless transmission of mote sensor data from the plurality of external sensors to the mote processor 81. Illustratively, FIG. 9*a* schematically shows a wireless external sensor 88 of the plurality of external sensors 89 having a transmitter for sending mote sensor data to the transceiver 83 of the mote module 80. As such, the wireless external sensor 88 can be positioned at any accommodating location near the illuminated display system 5 or the corresponding user. Moreover, the transceiver 83 further facilitates transmission of mote sensor data from the mote processor 81 to the module processor 65 and commands from module processor 65 master chipset to the slave set mote processor 81.

In one embodiment, as shown in FIGS. 7*d* and 9*a*, the mote module 80 is disposed within the receiving chamber 56 of the illuminated display system 5. In the operative position, the mote module 80 is coupled to at least one card interface 82. Each card interface 82 receives a corresponding interchangeable input/output or "daughter" card 87 to operatively interface with the mote processor 81.

At least one external sensor of the plurality of external sensors 89 is coupled to an interchangeable input/output card 87 that interfaces with the mote processor 81. A variety of external sensors, such as for example the external sensors described above, each functionally cooperate with corresponding daughter cards 87 such that each card 87 attaches to the illuminated display system 5 at a corresponding interface 82 to provide mote sensor data to the mote processor 81 and so that one card 87 can be interchanged for another card having a different external sensor for providing different mote sensor data. For example, each of the following external sensors for radioactivity detection, HazMat detection, chemical warfare agent detection, hazardous gas detection systems, air sample detection, and biological warfare agent detection are each functionally integrated with a corresponding daughter card 87 for insertion at the card interface 82.

The mote module 80 includes an analog-to-digital convertor 86. The analog-to-digital convertor 86 is coupled to the mote processor 81. The analog-to-digital convertor 86 is provided by the mote module 80 to accommodate external sensors 89 that provide analog signals to the mote module 80.

Figure 9B:
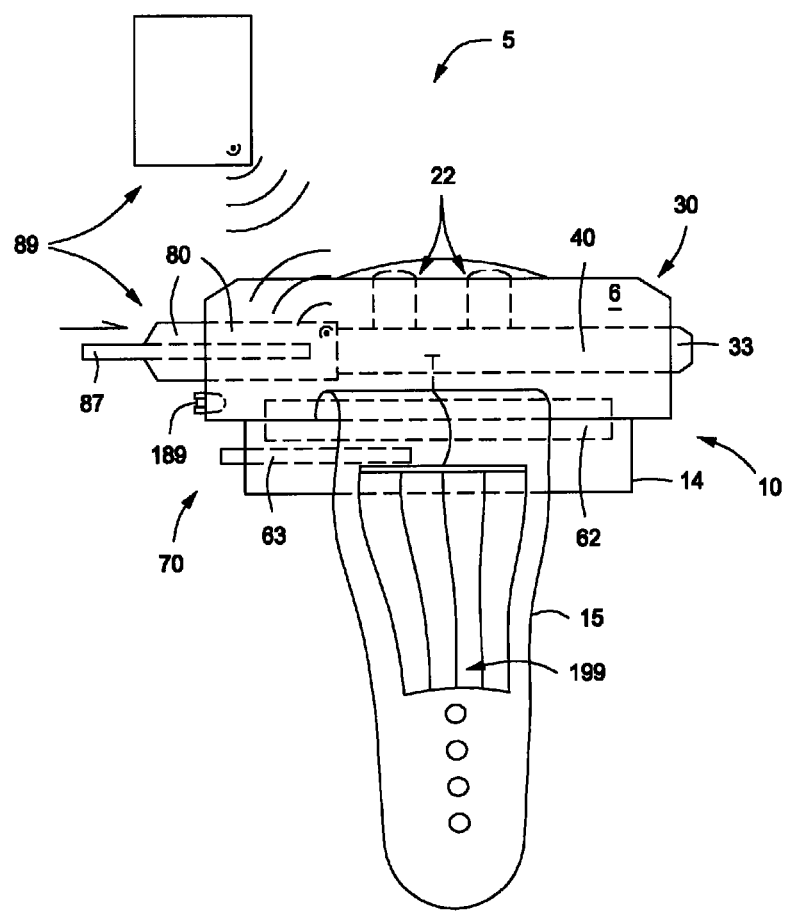
FIGS. 9b and 9c illustrate another embodiment of an illuminated display system with a fastening interface comprising wrist straps, with FIG. 9b as a side view and FIG. 9c as a top level view featuring at least one illumination membrane disposed on the wrist straps.
Figure 9C:
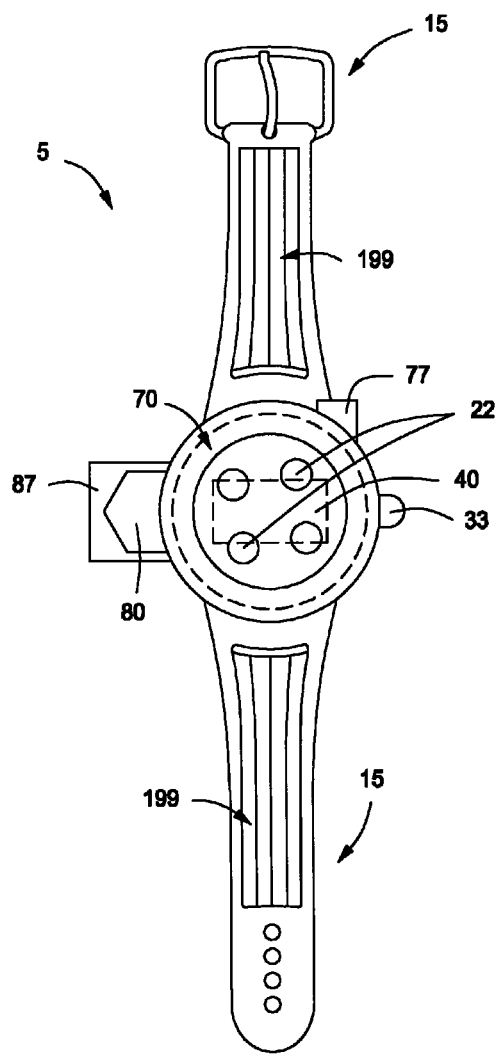

Generally, FIGS. 9b and 9c illustrate another embodiment of an illuminated display system 5 with the fastening interface 15 comprising wrist straps. The illuminated display system 5 includes an interface module 40, a base assembly 10 positioned below the interface module 40, and a dial assembly 30 positioned above the interface module 40. A plurality of light emitters is disposed on the interface module 40. As shown, the base assembly 10 includes a base body 14 and the dial assembly includes a dial body 6.

An operating subframe of the illuminated display system 5 provides a mote module 80. As shown, the mote module 80 is operatively coupled to the interface module 40. Similar to that described above, the interface module 40 includes a module processor, a memory unit, and at least one programming interface coupled to the module processor.

The base assembly 10 includes an electronic identification tag 63, disposed in the base body 14, similar to the electronic identification tag above. Moreover, a power source 65 is disposed in the base body 14 and electrically coupled to the interface module 40, the plurality of light emitters 22, and the operating subframe. Optionally, the base assembly 10 further includes an auxiliary input interface for either sending or receiving computer readable formatted files.

The illuminated display system 5 further includes a selector 33. As shown in the embodiment of FIG. 1, the selector 33 is electrically coupled to the interface module 40.

At least one external sensor of the plurality of external sensors 89 is coupled to an interchangeable input/output card 87 that interfaces with the mote module 80 of the operating subframe 70. A variety of external sensors, such as for example the external sensors described above, each functionally cooperate with corresponding daughter cards 87 such that each card 87 attaches to the illuminated display system 5 to provide mote sensor data to the mote module 80 and so that one card 87 can be interchanged for another card having a different external sensor for providing different mote sensor data.

Moreover, as shown in FIG. 9b, at least one external sensor of the plurality of external sensors comprises a wireless external sensor 88 of the plurality of external sensors 89 having a transmitter for sending mote sensor data to the transceiver 83 of the mote module 80. The wireless external sensor 88 can be positioned at any accommodating location near the illuminated display system 5 or the corresponding user. Illustratively, as the illuminated display system 5 is attached to a FEMA first responder's wrist, a wireless external sensor 88 comprising a wireless dosimeter is conveniently placed in the responder's clothing pocket to detect radioactive contamination within a disaster site. In one embodiment, the wireless external sensor 88 dosimeter comprises a floating-gate (FG) metal-oxide semiconductor field-effect transistor MOFSET based wireless dosimeter.

As shown in FIG. 9c, the operating subframe 70 further includes a removable external memory device 77. In one embodiment, among others, the removable external memory device 77 comprises a flash memory device. Illustratively, a combat medic in a battlefield triage setting attaches the illuminated display system 5 to an injured solider and makes and detailed audio recording of the medic's triage assessment. The resulting audio file is stored in the removable external memory device. Additionally, the medic inserts a wireless external sensor 88 in the soldier's pants' pocket to detect biohazardous agents within the surrounding environment.

The illuminated display system 5 of FIGS. 9c and 9b further includes at least one illumination membrane 199 disposed on the wrist straps. As shown, the at least one illumination membrane 199 is coupled to the interface module 40. The at least one illumination membrane 199 sends and receives signals to the interface module for operation thereof.

In one exemplary embodiment, as the selector 33 engages the interface module 40 to implement a lighting operation sequence to select a desired light emitter from the plurality of light emitters 22 and at least one illumination membrane 199 to emit a desired wavelength band of light. Illustratively, for the illuminated display system of FIGS. 9b and 9c, a first responder depresses the selector 33 to illuminate a red light emitter from the plurality of light emitters and at least one illumination membrane 199 is illuminated red, such as for FIG. 9c each illumination membrane 199 on each corresponding wrist strap 88 is illuminated red.

In one exemplary embodiment, as the selector 33 engages the interface module 40 to implement a lighting operation sequence to select a desired wavelength band of light by illuminating the at least one illumination membrane 199. Illustratively, for the illuminated display system of FIGS. 9b and 9c, a first responder depresses the selector 33 to illuminate a red wavelength band of visible light on at least one illumination membrane 199.

In one embodiment the at least one illumination membrane 199 comprises an organic semiconductor based illumination device. In another embodiment, the at least one illumination membrane 199 comprises a fiber optic based illumination device. In one embodiment, the at least one illumination membrane 199 comprises an optical modifier, for example, among others, a silicone membrane for receiving light from at least one light source, such as a light emitting diode. In one embodiment, the at least one illumination membrane 199 and the fastening interface 15 each comprise an optical modifier, for example, among others, a silicone membrane for receiving light from at least one light source, such as a light emitting diode.

Depending for example on the anticipated environmental threat, a first responder while assigning an illuminated display system to a burn victim triages and illuminates a yellow light emitter as well as replaces a chemical warfare agent detection daughter card 87 with a HazMat detection daughter card 87 to identify whether the victim will be contaminated with hazardous materials in route from the mass casualty site to a final care facility destination. In one exemplary embodiment of a lighting operation sequence, each of light emitters from the plurality of light emitters will illuminate for intermittent periods to indicate that the victim is contaminated with hazardous materials.

As the illuminated display system is activated by the first responder, such as while the first responder illuminates the yellow light emitter, a timer provided by the illuminated display system is started so that care providers at the final care facility destination are provided information relating to the total elapsed time since the injured user was first triaged. The first responder records voice notations of the victim at the scene with the selector 33 of the illuminated display system 5.

Moreover, the first responder positions the illuminated display system 5 near the victim's rf ID card or "dogtag" to capture the victim's personal data from the dogtag to the illuminated display system 5.

Accordingly, the resulting mote sensor data is collected by the module processor 65 via the mote processor 81, the identifier information is collected by the module processor 65 via the id tag processor 66, and the audio data and illuminated light emitter data is collected by the module processor 65 as well. Optionally, the module processor 65 stores the mote sensor data, identifier information, audio data, and illuminated light emitter data on the removable external memory device 77. In one embodiment, the module processor 65 combines illuminated light emitter data with mote sensor data from the mote module 80 to create an identification signal for transmission from the illuminated display system 5.

In one exemplary embodiment, one illuminated display system includes the following. A base assembly and a display interface coupled to the base assembly. The display interface includes a plurality of light emitters. Each light emitter provides information relating to a corresponding predetermined status of the user. Operatively, each desired light emitter is chosen for illumination thereof by a selector from the plurality of light emitters according to a lighting operation sequence.

The illuminated display system includes a dial assembly. The dial assembly includes an interface module and a selector coupled to the interface module. The interface module includes a module processor and a removable external memory device and a mote module each coupled to the module processor. The removable external memory device stores the lighting operation sequence and the illuminated light emitter data. The mote module is coupled to a plurality of external sensors for creating mote sensor data. The module processor combines illuminated light emitter data with mote sensor data from the mode module to create an identification signal for transmission from the illuminated display system.

With general reference to FIG. 9, an operation method for an operating subframe 70 of an illuminated display system 5 may be appreciated. The operating subframe 70 includes a module processor 65 and a memory unit 64a. The module processor 65 is coupled to a selector 33 and a plurality of light emitters 22.

Generally, the operating subframe 70 is powered on. From the memory unit 64a or, optionally, a removable external memory device 77, the last state is recalled from memory by the module processor 65. In one embodiment, the last state refers to the illumination status of at least one light emitter from the plurality of light emitters 22 just prior to loss of power of the illuminated display system 5. Specifically, before power loss, the light emitter was previously chosen for illumination thereof from the plurality of light emitters 22 via the selector 33 according to a lighting operation sequence whereby each light emitter provides a different predetermined wavelength of light than the other light emitters from the plurality of light emitters 22. Thus, each respective predetermined wavelength provides information relating to a corresponding predetermined status of the user that the illuminated display system 5 is assigned thereto. As such, the at least one light emitter from the plurality of light emitters 22 is illuminated according to the recalled last state.

Described in detail below, a low power clock sleep routine is initiated to extend functionality of the power source 62 coupled to the operating subframe 70. On receipt of a selector signal from the selector 33 by the module processor 65, the low power clock sleep routine is interrupted for the execution of lighting operation sequence. The lighting operation sequence, such as those exemplary lighting operation sequences discussed above, is then initiated. After execution of the lighting operation sequence, the low power consumption clock rate sleep routine is reestablished.

During the lighting operation sequence, a clock rate duration of the selector signal is determined by the module processor 65 coupled to the selector 33. In this disclosure and appended claims, the clock rate duration of the selector signal refers to the period by which the selector 33 is depressed by the illuminating user whereas the term selector signal refers to the electrical signal created by operating the selector 33. As such, based on a selector signal of a first duration, the selector operator advances the selection of light emitters from the plurality of light emitters 22. Based on a selector signal of a second duration, the user, such as the first responder, advances the selection of light emitters to turn of the illuminated light emitter and reactivate the lower power consumption clock rate sleep routine. Based on a selector signal of a third duration, the user advances the selection of light emitters to blink the illuminated light emitter.

To prevent an injured user from fraudulently changing their triage condition of the illuminated light emitter from the illuminated display system 5 set by the first responder to expedite injury care, one operation method for the operating subframe 70 features a lock function. Accordingly, based on selector signal of a first duration, the user, such as the first responder, advances the selection light emitters from the plurality of light emitters 22 to choose a desired light emitter for illumination as described above. To lock, however, the user then provides a selector signal of a fourth duration to lock the chosen light emitter from further selection of other light emitters from the plurality of light emitters 22. By providing a selector signal of a fifth duration, the user unlocks the chosen illuminated light emitter from further selection of other light emitters from the plurality of light emitters 22 such that lighting operation sequence is thus resumed. Optionally, in one embodiment, each selector signal may be of the same duration.

Illustratively, in one embodiment, the lock function prevents the injured user that is assigned to an illuminated display system 5 from changing the light color with a pushbutton selector 33. In particular, one initially presses the selector 33 to select the desired colored light for illumination. If no other color is selected over a predetermined period after initially selecting the desired colored light, for example three seconds elapses after selection of the desired colored light for illumination, the selector 33, according to the lighting operation sequence, provides a selector signal to lock the desired color from further selection. Once illuminating the locked-in chosen color, the selector 33 is pressed for three or more seconds to unlock lock the desired color. In other words, after providing a selector signal of a first duration to choose the desired color for illumination, the lighting operation sequence then provides a selector signal of a fourth duration to lock the chosen light emitter from further selection of other light emitters from the plurality of light emitters 22. In one embodiment, the first duration is equal to that of the forth duration. Once locked, in one embodiment, one must turn the illuminated display system 5 off and then back on again before selecting another color. As such, the illuminated display system 5 can be turned off by holding the selector for three more seconds while the illuminated color is in the locked position.

Figure 10:
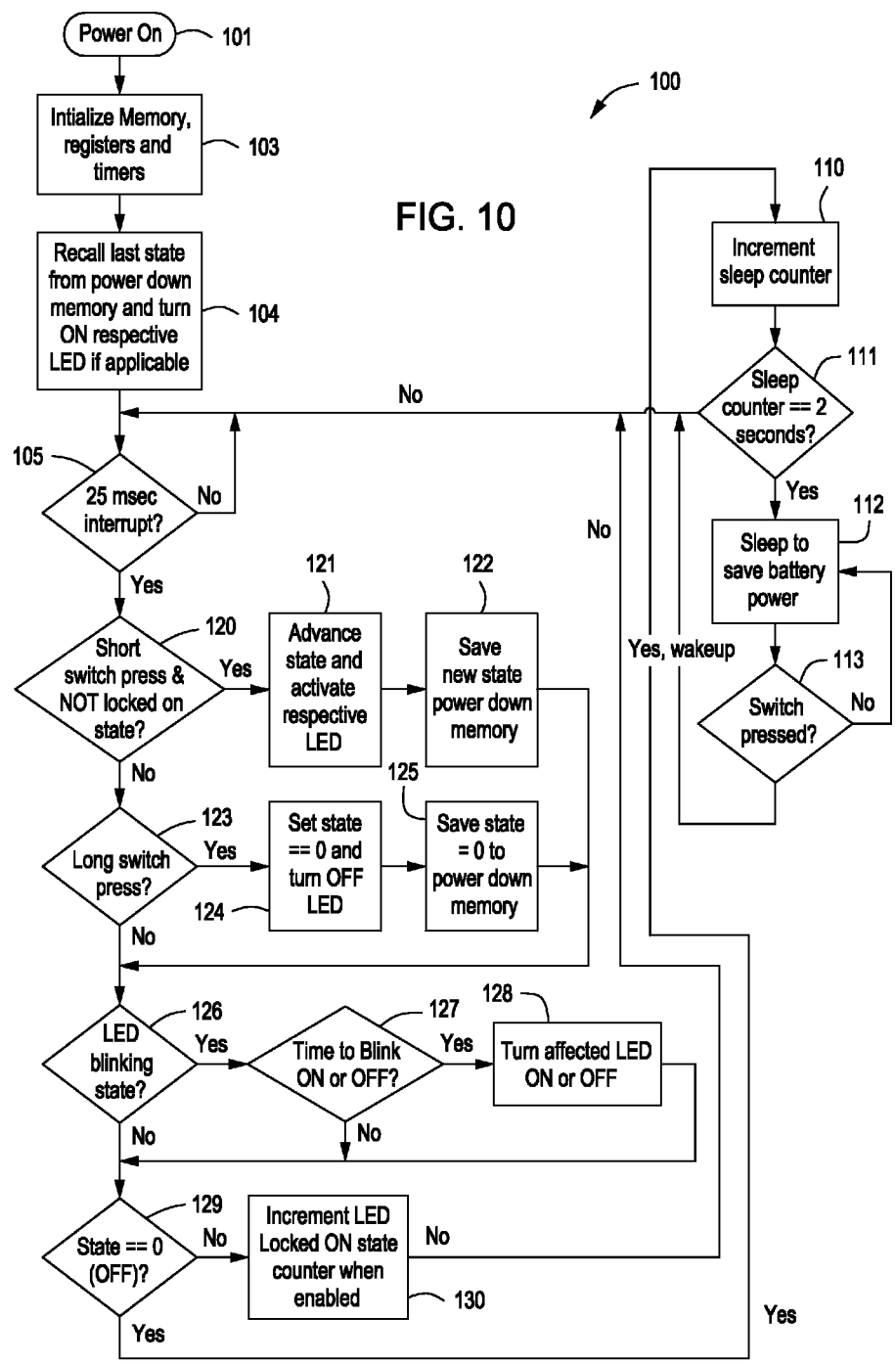
FIG. 10 is a flow diagram illustrating one operation method executed by an operating subframe.

FIG. 10 refers to a flow diagram illustrating one operation method 100 executed by an operating subframe 70. The operation method 100 of FIG. 10 generally shows, among others, a low power clock routine, at least one lighting operation sequence, and a last lit or last state memory recall routine.

Accordingly, the operation method 100 begins at step 101 with powering on an illuminated display system 5. In step 103, all registers, timers, and memory units and devices of the illuminated display system 5 are initialized. Step 104 is provided by the last lit memory recall routine. At step 104, the last state memory recall routine refers from the illuminated display system's 5 nonvolatile memory the illumination status of at least one light emitter from the plurality of light emitters 22 just prior to loss of power of the illuminated display system 5. Before power loss, the light emitter was previously chosen for illumination thereof by a selector 33 from the plurality of light emitters 22 according to a lighting operation sequence and, thus, information regarding the illuminated light emitter is stored in the illuminated display system's 5 memory such that each light emitter provides a different predetermined wavelength of light than the other light emitters from the plurality of light emitters 22. Each respective predetermined wavelength provides information relating to a corresponding predetermined status of the user that the illuminated display system 5 is assigned thereto. Illustratively, an injured soldier is triaged red by a combat medic and the appropriate light emitter on the illuminated display system 5 is lit such that in route to the hospital the illuminated display system 5 is dropped and temporary loses power. Upon powerup, the operation method 100 recalls from memory and reilluminates the previously chosen red light emitter.

The operation method 100 advances from step 104 to step 105 to establish the low power clock routine to extend battery cell life provided by the power source 62 by conserving power usage throughout the illuminated display system 5 while idling. Generally, steps 105, 110, 111, 112, and 113 are provided by the low power clock routine. The operation method 100 at step 105 initiates a clock cycle loop that awaits for an interruption over a period having a predetermined duration. In one embodiment, as illustratively shown, the loop specifically awaits an interrupt greater than 25 milliseconds in the form of depressing the selector 33 for more than 25 milliseconds. If the clock cycle loop surpasses a predetermined wait period without an interrupt in step 111, then the operation method 100 engages the illuminated display system 5 in an idle or sleep mode at step 112 to conserve power.

If the sleep cycle is interrupted, say by pressing the selector 33 at step 113, the operation method 100 returns to step 105 to determine whether the selector 33 depression endures beyond a predetermined period, such as beyond 25 milliseconds. Accordingly, if the selector depression interruption is beyond the predetermined period, the clock cycle loop advances from step 105 to initiate one exemplary illumination operation sequence beginning at step 120. In general, steps 120, 121, 122, 123, 124, 125, 126, 127, 128, 129, and 130 are provided by the illustrative illumination operation sequence. As discussed above, it should be added the illuminated display system 5 features a programming interface 67 for reprogramming the illuminating operation sequence for the illuminated display system 5.

With reference to FIG. 10, steps 120, 121 and 122 enable the illuminated display system 5 operator to advance the selection of light emitters based on a selector signal of a first duration to chose one light emitter for illumination and store the light emitter selection in at least the memory unit 64a. Steps 123, 124, and 125 enable an operator to advance the selection of light emitters based on a selector signal of a second duration to turn off the illuminated light emitter and store that selection in at least the memory unit 64a. Steps 126, 127, 128 permit advancement of the selection of light emitter based on a selector signal of a third duration to either select or deselect a blinking aspect of the illuminated light emitter and store the selection in at least the memory unit 64a.

Steps 129 and 130 provide a lock function similar to that discussed above. After providing a selector signal of a first duration to choose the desired light emitter for illumination, one then provides a selector signal of a fourth duration at step 129 to lock the chosen light emitter from further selection of other light emitters from the plurality of light emitters 22. Optionally, in one embodiment, each selector signal may be of the same duration. Illustratively, in one embodiment, the first duration is equal to that of the fourth duration.

Figure 12:
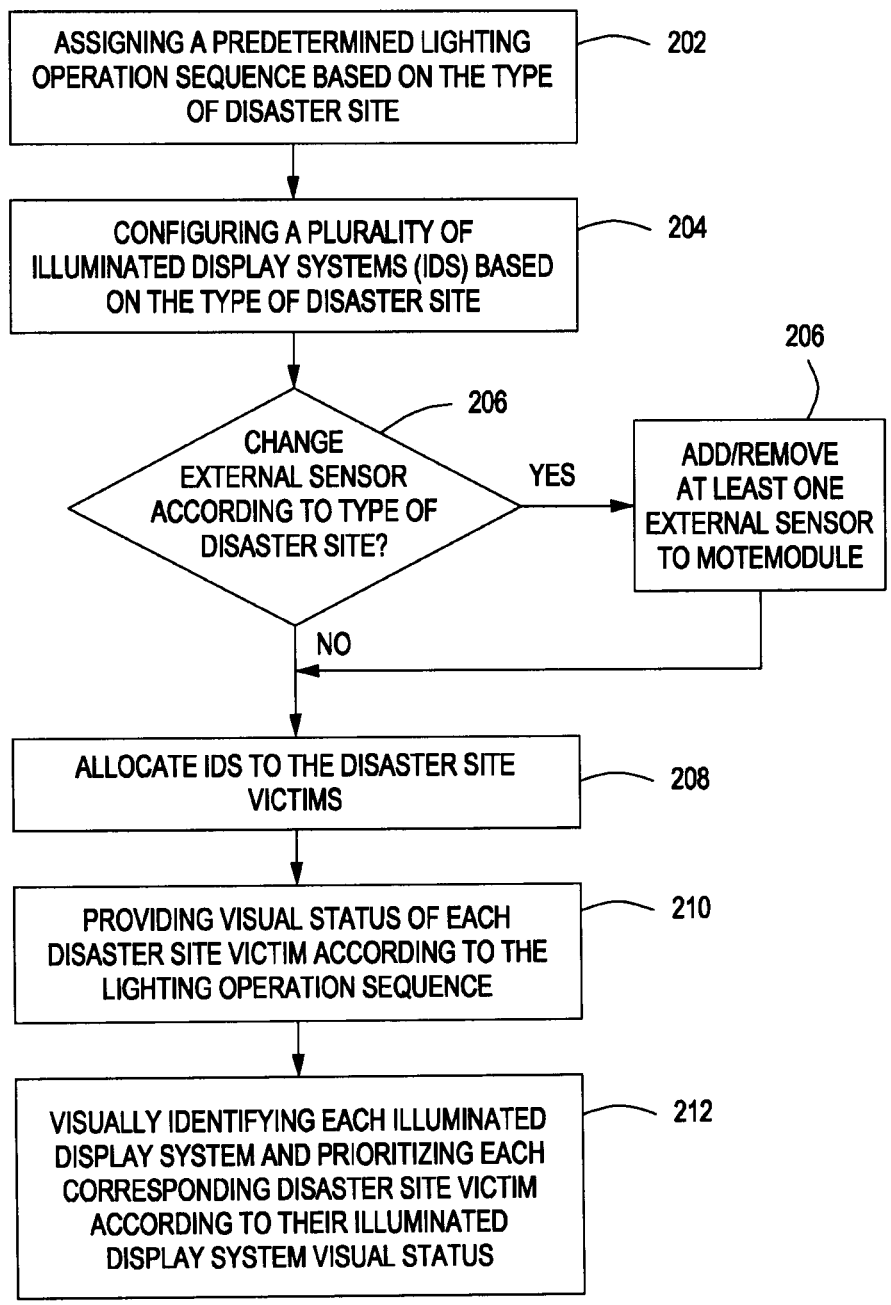
FIG. 12 is a follow diagram illustrating a method for visually tracking disaster site victims.

Referring to FIG. 12, a method for visually tracking disaster site victims 200 may be appreciated as follows. In step 202, based on the type of disaster site, a predetermined lighting operation sequence is assigned and, in step 204, a plurality of illuminated display systems are configured based on the type of disaster site. The plurality of illuminated display systems are similar to those illuminated display systems described above.

In one embodiment, the same predetermined lighting operation sequence is applied to any type of disaster site. In one embodiment, a lighting operation sequence is predetermined to operatively illuminate the illuminated display system for each type natural disaster, for example a separate lighting operation sequence is assigned for an earthquake, volcano, hurricane, tornado, blizzard, fire, tsunami, and flood, among others. In another embodiment, a lighting operation sequence is assigned for all natural disasters and another lighting operation sequence is assigned for all man-made disasters, such as an act of terrorism; battlefield scenario; crime spree; a nuclear, chemical or hazardous materials crisis; and a biological agent scenario, among others.

Illustratively, FEMA issues a warning based on an impending natural disaster such as a hurricane or earthquake where first responders and victims alike were previously educated on various procedures according to an established disaster plan. One embodiment of a disaster plan and corresponding predetermined lighting operation sequence assigns gender status to first responder visual location of surviving disaster site victims, such as the color "red" is assigned to children, "green" for women, "blue" for men and "yellow" for animals. Moreover, the disaster plan optionally assigns health status of each disaster site victim in addition to gender status, such as alternating illuminated lights indicate a disaster site victim in critical health, intermittent illuminated lights indicate healthy disaster site victims, and solid lights indicate a non-surviving victims. Accordingly, the illuminated display system visually provides a plurality of status conditions based on the assigned predetermined lighting operation sequence. Those of ordinary skill in the art will readily recognize that the selected predetermined lighting operation sequence based the corresponding established disaster plan for that type of disaster site may include any combination of continuous, alternating or intermittently illuminated light emissions at various wavelengths.

Optionally, the method for visually tracking disaster site victims 200 continues with step 206 whereby at least one external sensor provides is added, as needed, to the mote module. The at least one external sensor provides mote sensor data that is relevant to the type of disaster in which the illuminated display system is deployed.

Illustratively, in assessing the first responder needs for an oil spill disaster, a FEMA director orders that Hazmat water detection sensors and hazardous gas detection external sensors, in a combination of wireless external sensors or interchangeable daughter card external sensors, be added to the mote module of each illuminated display system. Thereafter, in response to a subsequent earthquake and associated nuclear crises, the FEMA director orders that the removal of HazMat water detection sensors from each illumined display system and the addition of radioactive dosimeters sensors to each mote module for assisting first responders at the subsequent earthquake disaster site.

In step 208, the method 200 requires that the plurality of illuminated display systems are allocated to the disaster site victims. In one embodiment, FEMA implemented public programs for allocating basic models of illuminated display systems to residents in areas having a high probability of disaster, for example FEMA would provide vouchers for the purchase of illumined display systems to participating residents in the "ring of fire" (i.e. earthquake, tsunami, and volcano)—prone west coast of the United States. In another embodiment, first responders directly distribute the plurality of illuminated display systems at the disaster site.

In step 210, each disaster site victim provides visual status to first responders with their corresponding illumined display system according to the lighting operation sequence. The visual status includes illuminating at least one light emitter from the corresponding illuminated display system according to the lighting operation sequence. In one embodiment, the illuminated at least one light emitter may be a combination of visible and infrared light emitters. In one embodiment, a power source provided by each illuminated display system supplies power to illuminated the at least one light emitter for 15 days.

In the disaster site, a first responder in step 212 visually identifies each illuminated display system and prioritizes rescue of each corresponding disaster site victim according to their illuminated display system visual status. Illustratively, with the use of illumined display systems, the method for visually tracking disaster site victims promotes visual search and rescue operations during the night as well as the daytime. In mission critical conditions, FEMA managers use the visual status from the plurality of illuminated display systems to observe and note areas where disaster site victims are located for 24 hours a day to thereby enhance the likelihood of disaster site victim survivability for those victims using their assigned illuminated display systems.

Although the present invention has been described in detail, it should be understood that various changes, substitutions, and alterations could be made hereto without departing from the spirit and scope of the invention as defined by the appended claims.

I claim:

1. An interface module for a display interface of an illuminated display system, comprising:
a selector; and
an operating subframe,
  the operating subframe coupled to the selector and to a plurality of light emitters provided by the display interface,
    each light emitter providing a different predetermined wavelength of light than the other light emitters from the plurality of light emitters,
    each respective predetermined wavelength providing information relating to a corresponding predetermined status of the user,
      each desired light emitter is chosen, by the selector for illumination, from the plurality of light emitters according to a lighting operation sequence, the operating subframe includes a module processor coupled to the plurality of light emitters and the selector, a removable external memory device, an external memory processor, and a bus coupled to the module processor and the removable external memory processor,
      the module processor stores illuminated light emitter information in a computer readable format within the removable external memory device.

2. The interface module according to claim 1 wherein the external memory processor includes an external transceiver and wherein the eternal memory processor is wirelessly coupled to the removable external memory device via the transceiver.

3. The interface module according to claim 1 further comprising a programming interface, the programming interface coupled to the module processor and wherein the programming interface provides at least one reprogrammed lighting operating sequence to the plurality of light emitters via the module processor.

4. The interface module according to claim 1 further comprising an id tag processor, the id tag processor coupled to the module processor via the bus.

5. The interface module according to claim 4 wherein the id tag processor includes a radio frequency (rf) id processor, a transceiver for accommodating rf signals and a tag memory unit.

6. The interface module according to claim 5 wherein the module processor combines illuminated light emitter data with identifier information from the id tag processor to create an identification signal for transmission from the illuminated display system.

7. The interface module according to claim 1 further comprising a mote module, the mote module coupled to the module processor via the bus.

8. The interface module according to claim 7 wherein the mote module includes a mote processor.

9. The interface module according to claim 8 wherein mote processor is coupled to a plurality of external sensors.

10. The interface module according to claim 8 wherein the mote module further includes an analog-to-digital convertor coupled to the mote processor and wherein at least one external sensor is coupled to the analog-to-digital convertor.

11. The interface module according to claim 10 wherein one external sensor of the plurality of external sensors is coupled to an interchangeable input/output card that interfaces with the mote processor.

12. An illuminated display system comprising:
a base assembly;
a display interface coupled to the base assembly,
  the display interface including a plurality of light emitters,
    each light emitter providing a different predetermined wavelength of light than the other light emitters from the plurality of light emitters,
    each respective predetermined wavelength providing information relating to a corresponding predetermined status of the user,
      each desired light emitter is chosen for illumination thereof by the selector from the plurality of light emitters according to a lighting operation sequence; and
a dial assembly including an interface module and selector coupled to the interface module,
  the interface module including a module processor, a removable external memory device, and a mote module,
  the external memory unit stores the lighting operation sequence and illuminated light emitter data, and the mote module is coupled to a plurality of external sensors for creating mote sensor data therefrom, the module processor combines illuminated light emitter data with mote sensor data from the mote module to create an identification signal for transmission from the illuminated display system.

13. The illuminated display system according to claim 12 wherein the lighting operation sequence comprises a user's triage status for illuminating the plurality of light emitters selected from the group consisting of: a red wavelength band of light, a yellow wavelength band of light, a green wavelength band of light, a blue wavelength band of light, a purple wavelength band of light, and a black wavelength band of light.

14. An operation method for an operating subframe of an illuminated display system, the operating subframe including module processor and a memory unit, the module processor coupled to a plurality of light emitters, the operating method comprising the steps of:

powering on the operating subframe;
recalling last state from the memory unit;
illuminating the light emitter according to the last state,
the light emitter previously chosen for illumination thereof by a selector from the plurality of light emitters according to a lighting operation sequence,
each light emitter providing a different predetermined wavelength of light than the other light emitters from the plurality of light emitters,
each respective predetermined wavelength providing information relating to the predetermined status of the user;
initiating low power consumption clock rate sleep routine;
interrupting, on receipt of a selector signal by the module processor, the low power consumption clock rate sleep routine for the lighting operation sequence; and
reestablishing the low power consumption clock rate sleep routine.

15. The operation method according to claim 14 further comprising the step of determining a clock rate duration of the selector signal.

16. The operation method according to claim 15 further comprising the step of advancing the selection of light emitters, based on a selector signal of a first duration, to choose one light emitter for illumination.

17. The operation method according to claim 16 further comprising the step of advancing the selection of light emitters, based on a selector signal of a second duration, to turn off the illuminated light emitter.

18. The operation method according to claim 17 further comprising the step of advancing the selection of light emitters, based on a selector signal of a third duration, to blink the illuminated light emitter.

19. A method for visually tracking disaster site victims comprising the steps of:
assigning a predetermined lighting operation sequence based on the type of disaster site;
configuring a plurality of illuminated display systems based on the type of disaster site,
each illuminated display system includes a plurality of light emitters,
each light emitter providing a different predetermined wavelength of light than the other light emitters from the plurality of light emitters,
each respective predetermined wavelength providing information relating to a corresponding predetermined status of the user,
each desired light emitter is chosen for illumination thereof by a selector from the plurality of light emitters according to the lighting operation sequence, and
an interface module, the interface module coupled to selector,
the interface module including a module processor, a removable external memory device, and a mote module,
the external memory unit stores the lighting operation sequence and illuminated light emitter data, and
the mote module is coupled to the removable external memory device and to a plurality of external sensors,
the mote module creating mote sensor data from data received by the plurality of external sensors;
adding, as needed, at least one external sensor to the mote module,
the at least one external sensor provides mote sensor data that is relevant to the type of disaster site in which the illuminated display system is deployed;
allocating the plurality of illuminated display systems to the disaster site victims;
providing visual status of each disaster victim according to the lighting operation sequence with each correspondingly assigned illuminated display system,
the visual status including illuminating at least one light emitter from the corresponding illuminated display system according to the lighting operation sequence; and
visually identifying each illumined display system in the disaster site and prioritizing each corresponding disaster site victim according to their illuminated display system visual status.

20. A method for visually tracking disaster site victims comprising the steps of:
assigning a predetermined lighting operation sequence based on the type of disaster site;
configuring a plurality of illuminated display systems based on the type of disaster site,
each illuminated display system includes a plurality of light emitters,
each light emitter providing a different predetermined wavelength of light than the other light emitters from the plurality of light emitters,
each respective predetermined wavelength providing information relating to a corresponding predetermined status of the user,
each desired light emitter is chosen for illumination thereof by a selector from the plurality of light emitters according to the lighting operation sequence, and
an interface module, the interface module coupled to selector,
the interface module including a module processor and a removable external memory device,
the external memory unit stores the lighting operation sequence and illuminated light emitter data;
allocating the plurality of illuminated display systems to the disaster site victims;
providing visual status of each disaster victim according to the lighting operation sequence with each correspondingly assigned illuminated display system, the visual status including illuminating at least one light emitter from the corresponding illuminated display system according to the lighting operation sequence; and visually identifying each illumined display system in the disaster site and prioritizing each corresponding disaster site victim according to their illuminated display system visual status.

* * * * *

UNITED STATES PATENT AND TRADEMARK OFFICE
CERTIFICATE OF CORRECTION

PATENT NO.        : 8,744,871 B1
APPLICATION NO.   : 13/098405
DATED             : June 3, 2014
INVENTOR(S)       : Juan Enrique Cienfuegos It is certified that error appears in the above-identified patent and that said Letters Patent is hereby corrected as shown below:

In the Drawings

In Figure 9B the arrow head above reference numeral 87 is corrected to reflect the arrow in the originally submitted hand drawings.

In Figure 9C the reference indicator line has been corrected to reflect the indicator line in the originally submitted hand drawings.

In Figure 12 the typographical error indicating "ILUMINATED DISPLAY" has been amended to indicate proper spelling "ILLUMINATED DISPLAY" as shown in Step 204.

In the Specification

Column 10, line 7, delete "the module processor." and substitute with -- the module processor 151. --.

Column 14, lines 16 - 17, delete "applying a compressive force against an in injured user." and substitute with -- applying a compressive force against an injured user. --.

Column 19, lines 13 - 14, delete "a battery assisted passive REID tag and an ultra high frequency passive RFID tag." and substitute with -- a battery assisted passive RFID tag, and an ultra high frequency passive RFID tag. --.

Column 30, line 20, delete "in the soldier's pants' pocket" and substitute with -- in the soldier's pants pocket --.

Signed and Sealed this
Nineteenth Day of August, 2014

Michelle K. Lee
*Deputy Director of the United States Patent and Trademark Office*

In the Claims

Column 43, lines 1 - 3, cancel the following text to correct the typographical error for the word "eternal":
"2. The interface module according to Claim 1 wherein the external memory processor includes an external transceiver and wherein the eternal memory processor is wirelessly coupled to the removable external memory device via the transceiver."

and insert with the following Claim:

-- 2. The interface module according to Claim 1 wherein the external memory processor includes an external transceiver and wherein the external memory processor is wirelessly coupled to the removable external memory device via the transceiver. --.

Columns 45 - 46, for Claim 14, please correct the antecedent term from "recalling last state from the memory unit;" to "recalling a last state from the memory unit;" by cancelling the following text:
"14. An operation method for an operating subframe of an illuminated display system, the operating subframe including module processor and a memory unit, the module processor coupled to a plurality of light emitters, the operating method comprising the steps of:
powering on the operating subframe;
recalling last state from the memory unit;
illuminating the light emitter according to the last state,
the light emitter previously chosen for illumination thereof by a selector from the plurality of light emitters according to a lighting operation sequence,
each light emitter providing a different predetermined wavelength of light than the other light emitters from the plurality of light emitters,
each respective predetermined wavelength providing information relating to the predetermined status of the use user;
initiating low power consumption clock rate sleep routine;
interrupting, on receipt of a selector signal by the module processor, the low power consumption clock rate sleep routine for the lighting operation sequence; and
reestablishing the low power consumption clock rate sleep routine."

and insert with the following Claim:

-- 14. An operation method for an operating subframe of an illuminated display system, the operating subframe including module processor and a memory unit, the module processor coupled to a plurality of light emitters, the operating method comprising the steps of:
powering on the operating subframe;
recalling a last state from the memory unit;

illuminating the light emitter according to the last state,
the light emitter previously chosen for illumination thereof by a selector from the plurality of light emitters according to a lighting operation sequence,
each light emitter providing a different predetermined wavelength of light than the other light emitters from the plurality of light emitters,
each respective predetermined wavelength providing information relating to the predetermined status of the user;
initiating low power consumption clock rate sleep routine;
interrupting, on receipt of a selector signal by the module processor, the low power consumption clock rate sleep routine for the lighting operation sequence; and
reestablishing the low power consumption clock rate sleep routine. --.

Columns 46 - 48, for Claim 19, please correct the antecedent term from "the interface module, the interface module coupled to selector" to "the interface module, the interface module coupled to the selector" by cancelling the following text:
"19. A method for visually tracking disaster site victims comprising the steps of;

assigning a predetermined lighting operation sequence based on the type of disaster site;

configuring a plurality of illuminated display systems based on the type of disaster site, each illuminated display system includes a plurality of light emitters,
each light emitter providing a different predetermined wavelength of light than the other light emitters from the plurality of light emitters,
each respective predetermined wavelength providing information relating to a corresponding predetermined status of the user,
each desired light emitter is chosen for illumination thereof by a selector from the plurality of light emitters according to the lighting operation sequence, and
an interface module, the interface module coupled to selector,
the interface module including a module processor, a removable external memory device, and a mote module,
the external memory unit stores the lighting operation sequence and illuminated light emitter data, and the mote module is coupled to the removable external memory device and to a plurality of external sensors,
the mote module creating mote sensor data from data received by the plurality of external sensors;

adding, as needed, at least one external sensor to the mote module,
the at least one external sensor provides mote sensor data that is relevant to the type of disaster site in which th in which the illuminated display system is deployed;

allocating the plurality of illuminated display systems to the disaster site victims;

providing visual status of each disaster victim according to the lighting operation sequence with each correspondingly assigned illuminated display system, the visual status including illuminating at least one light emitter from the corresponding illuminated display system according to the lighting operation sequence; and visually identifying each illumined display system in the disaster site and prioritizing each corresponding disaster site victim according to their illuminated display system visual status."

and insertig with the following Claim:

-- 19. A method for visually tracking disaster site victims comprising the steps of:

assigning a predetermined lighting operation sequence based on the type of disaster site;

configuring a plurality of illuminated display systems based on the type of disaster site, each illuminated display system includes a plurality of light emitters,
each light emitter providing a different predetermined wavelength of light than the other light emitters from the plurality of light emitters,
each respective predetermined wavelength providing information relating to a corresponding predetermined status of the user,
each desired light emitter is chosen for illumination thereof by a selector from the plurality of light emitters according to the lighting operation sequence, and
an interface module, the interface module coupled to the selector,
the interface module including a module processor, a removable external memory device, and a mote module,
the external memory unit stores the lighting operation sequence and illuminated light emitter data, and
the mote module is coupled to the removable external memory device and to a plurality of external sensors,
the mote module creating mote sensor data from data received by the plurality of external sensors;

adding, as needed, at least one external sensor to the mote module,
the at least one external sensor provides mote sensor data that is relevant to the type of disaster site in which the illuminated display system is deployed;

allocating the plurality of illuminated display systems to the disaster site victims;

providing visual status of each disaster victim according to the lighting operation sequence with each correspondingly assigned illuminated display system,
the visual status including illuminating at least one light emitter from the corresponding illuminated display system according to the lighting operation sequence; and
visually identifying each illumined display system in the disaster site and prioritizing each corresponding disaster site victim according to their illuminated display system visual status. --.

CERTIFICATE OF CORRECTION (continued)
U.S. Pat. No. 8,744,871 B1

Column 28, line 24 (last line), for the following typographical numerical error correcting Claim "19." to "20.", respectfully delete "19. A method for visually tracking disaster site victims" and substitute with -- 20. A method for visually tracking disaster site victims --.